(12) United States Patent
D'Elia

(10) Patent No.: US 7,033,824 B2
(45) Date of Patent: *Apr. 25, 2006

(54) KETOGULONIGENIUM SHUTTLE VECTORS

(75) Inventor: John D'Elia, Champaign, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 159 days.

This patent is subject to a terminal disclaimer.

(21) Appl. No.: 09/826,206

(22) Filed: Apr. 5, 2001

(65) Prior Publication Data

US 2002/0039761 A1 Apr. 4, 2002

Related U.S. Application Data

(60) Provisional application No. 60/194,625, filed on Apr. 5, 2000.

(51) Int. Cl.
*C12N 15/00* (2006.01)
*C12N 1/12* (2006.01)
*C07H 21/02* (2006.01)

(52) U.S. Cl. .................... 435/320.1; 435/4; 435/6; 435/69.1; 435/183; 435/252.3; 536/23.1

(58) Field of Classification Search ............ 435/320.1, 435/252.3, 69.1, 471, 476–488, 490, 252–3; 536/23.2–23.7; 530/350
See application file for complete search history.

(56) References Cited

U.S. PATENT DOCUMENTS

| | | | |
|---|---|---|---|
| 2,421,611 A | 6/1947 | Gray | 195/47 |
| 3,043,749 A | 7/1962 | Huang | 195/47 |
| 3,234,105 A | 2/1966 | Motizuki et al. | 195/49 |
| 3,907,639 A | 9/1975 | Makover et al. | 195/36 R |
| 3,912,592 A | 10/1975 | Makover et al. | 195/31 R |
| 4,876,195 A | 10/1989 | Shirafuji et al. | 435/137 |
| 4,877,735 A | 10/1989 | Nogami et al. | 435/138 |
| 4,892,823 A | 1/1990 | Imai et al. | 435/138 |
| 4,933,289 A | 6/1990 | Imai et al. | 435/253.3 |
| 4,935,359 A | 6/1990 | Yin et al. | 435/138 |
| 4,945,048 A | 7/1990 | Uchihori et al. | 435/105 |
| 4,960,695 A | 10/1990 | Hoshino et al. | 435/42 |
| 4,994,382 A | 2/1991 | Ameyama et al. | 435/119 |
| 5,082,785 A | 1/1992 | Manning et al. | 435/252.32 |
| 5,312,741 A | 5/1994 | Hoshino et al. | 435/42 |
| 5,344,768 A | 9/1994 | Urakami | 435/119 |
| 5,399,496 A | 3/1995 | Fujiwara et al. | 435/320.1 |
| 5,437,989 A | 8/1995 | Asakura et al. | 435/190 |
| 5,474,924 A | 12/1995 | Nogami et al. | 435/138 |
| 5,541,108 A | 7/1996 | Fujiwara et al. | 435/252.1 |
| 5,580,782 A | 12/1996 | Beppu et al. | 435/252.1 |
| 5,834,231 A | 11/1998 | Stoddard et al. | 435/42 |
| 5,989,891 A | 11/1999 | Liaw et al. | 435/244 |
| 6,127,156 A | 10/2000 | Hoshino et al. | 435/189 |
| 6,127,174 A | 10/2000 | Tonouchi et al. | 435/320.1 |
| 6,316,231 B1 | 11/2001 | Stoddard et al. | 435/138 |
| 6,319,699 B1 | 11/2001 | Stoddard et al. | 435/138 |
| 6,503,748 B1 * | 1/2003 | Schmidt et al. | 435/252.3 |

FOREIGN PATENT DOCUMENTS

| | | |
|---|---|---|
| EP | 0 206 471 B1 | 12/1986 |
| EP | 0 213 591 B1 | 3/1987 |
| EP | 0 221 707 B1 | 5/1987 |
| EP | 0 276 832 A2 | 8/1988 |
| EP | 0 278 447 B1 | 8/1988 |
| EP | 0 276 832 A3 | 7/1989 |
| EP | 0 381 027 A | 8/1990 |
| EP | 0 518 136 A2 | 12/1992 |
| EP | 0 518 136 A3 | 3/1994 |
| EP | 0 832 974 A2 | 4/1998 |
| EP | 0 832 974 A3 | 11/1999 |
| EP | 1 076 094 A2 | 2/2001 |
| JP | 41-159 | 1/1966 |
| JP | 41-160 | 1/1966 |
| JP | 41-5907 | 3/1966 |
| JP | 59-113896 | 6/1984 |
| SU | 526660 | 10/1976 |
| WO | WO 98/17819 A1 | 4/1998 |
| WO | WO 98/17819 A3 | 4/1998 |
| WO | WO 98/33885 A1 | 8/1998 |
| WO | WO 98/33885 A3 | 8/1998 |
| WO | WO 00/15827 A2 | 3/2000 |
| WO | WO 00/15827 A3 | 7/2000 |

OTHER PUBLICATIONS

Chen, B.P., and Hai, T., "Expression vectors for affinity purification and radiolabeling of proteins using *Escherichia coli* as host," *Gene 139*:73-79, Elsevier Science B.V. (1994).

Delic, V., et al., "Microbial Reactions for the Synthesis of Vitamin C (L-Ascorbic Acid)," in *Biotechnology of Vitamins, Pigments and Growth Factors*, Vandamme, E.J., ed., Elsevier Applied Science (London & New York) pp. 299-336 (1989).

(Continued)

*Primary Examiner*—Manjunath N. Rao
(74) *Attorney, Agent, or Firm*—Kirkpatrick & Lockhart Nicholson Graham LLP

(57) ABSTRACT

The present invention relates, in general, to vectors comprising *Ketogulonigenium* replicons. More specifically, the present invention relates to vectors comprising a *Ketogulonigenium* replicon found on the endogenous plasmid contained in Deposit No. NRRL B-30035.

47 Claims, 12 Drawing Sheets

OTHER PUBLICATIONS

Lonsdale, D.M., et al., "pFC1 to pFC7: A novel family of combinatorial cloning vectors," *Plant Biol. Reporter* 13:343-345, Transaction Periodicals Consortium (1995).

Messing, J., "New M13 Vectors for Cloning," *Methods Enzymol.* 101:20-78, Academic Press, Inc. (1983).

Payne, M.S., and Jackson, E.N., "Use of Alkaline Phosphatase Fusions To Study Protein Secretion in *Bacillus subtilis,*" *J. Bacteriol.* 173:2278-2282, American Society for Microbiology (1991).

Simon, R., et al., "A Broad Host Range Mobilization System for *In Vivo* Genetic Engineering: Transposon Mutagenesis in Gram Negative Bacteria," *Bio/Technol.* 1:784-791, Nature Publishing Company (1983).

Sugisawa, H., et al., "Microbial Production of 2-Keto-L-Gulonic Acid from L-Sorbase and D-Sorbitol by *Gluconobacter melanogenus,*" *Agric. Biol. Chem.* 54:1201-1209, Japan Society for Bioscience, Biotechnology, and Agrochemistry (1990).

Wunderlich, M., and Glockshuber, R., "*In Vivo* Control of Redox Potential during Protein Folding Catalyzed by Bacterial Protein Disulfide-isomerase (DsbA)," *J. Biol. Chem.* 268:24547-24550, American Society for Biochemistry and Molecular Biology, Inc. (1993).

Urbance, J.W. et al., "Taxonomic characterization of *Ketogulonigenium vulgare* gen. nov., sp., nov. and *Ketogulonigenium robustum* sp. nov., which oxidize L-sorbase to 2-keto-L-gulonic acid," *Int. J. Systematic Evol. Microbiol.* 51:1059-1070, Society for General Microbiology (May 2001).

U.S. Appl. No. 09/826,205, filed Apr. 5, 2001, Schmidt et al.

U.S. Appl. No. 09/826,191, filed Apr. 5, 2001, D'Elia, J. et al.

Altschul, S.F., et al., "Gapped BLAST and PSI-BLAST: a new generation of protein database search programs," *Nucl. Acids Res.* 25:3389-3402, Oxford University Press (1997).

Ameyama, M., et al., "Existence of a Novel Prosthetic Group, PQQ, in Membrane-Bound, Electron Transport Chain-Linked, Primary Dehydrogenases of Oxidative Bacteria," *FEBS Lett.* 130:179-183, Elsevier/North-Holland Biomedical Press (1981).

Bishop, A., et al., "Pyrroloquinoline Quinone: A Novel Vitamin?," *Nutrition Rev.* 56:287-293, International Life Sciences Institute (1998).

Dekker, R.H., et al., "Covalent Addition of $H_2O$, Enzyme Substrates and Activators to Pyrrolo-quinoline Quinone, the Coenzyme of Quinoproteins," *Eur. J. Biochem.* 125:69-73, Springer-Verlag (1982).

Follettie, M.T., "DNA Technology for *Corynebacterium glutamicum*: Isolation and Characterization of Amino Acid Biosynthetic Genes," Ph.D. Thesis, Massachusetts Institute of Technology (1989).

Galanos, C., et al., "A New Method for the Extraction of R Lipopolysaccharides," *Eur. J. Biochem.* 9:245-249, Springer-Verlag (1969).

Helsinki, D.R., et al., "Replication Control and Other Stable Maintenance Mechanisms of Plasmids," Ch. 122 in *Escherichia coli and Salmonella: Cellular and Molecular Biology*, vol. 2, 2nd edition, Neidhardt, F.C., ed., ASM Press, Washington, D.C., pp. 2295-2324 (1996).

Kieslich, K., "Biotransformations," *Biotechnology—A Comprehensive Treatise in 8 Volumes*, vol. 6A:436-437, Verlag Chemie, Deerfield Beach, Florida (1984).

Martin, C.K.A., and Perlman, D., "Conversion of *L*-Sorbase to 2-Keto-*L*-gulonic Acid by Mixtures of Immobilized Cells of *Gluconobacter melanogenus* IFO 3293 and *Pseudomonas* Species," *Eur. J. Appl. Microbiol.* 3:91-95, Springer-Verlag (1976).

Morrison, D.A., "Transformation in *Escherichia coli*: Cryogenic Preservation of Competent Cells," *J. Bacteriol.* 132:349-351, American Society for Microbiology (1977).

Pearson, W.R., and Lipman, D.J., "Improved tools for biological sequence comparison," *Proc. Natl. Acad. Sci. USA* 85:2444-2448, National Academy of Sciences of the USA (1988).

Pelczar, M.J., Jr., and Reid, R.D., "Methods of Isolating Pure Cultures," in *Microbiology*, Pelczar, M.J., Jr., and Reid, R.D., eds., McGraw-Hill Book Company, Inc., New York, NY, pp. 140, first page of chapter 3, and 930 (1972).

Qureshi, N., et al., "Location of Fatty Acids in Lipid A Obtained from Lipopolysaccharide of *Rhodopseudomonas sphaeroides* ATCC 17023," *J. Biol. Chem.* 263:5502-5504, The American Society for Biochemistry and Molecular Biology, Inc. (1988).

Qureshi, N., et al., "Position of Ester Groups in the Lipid A Backbone of Lipopolysaccharides Obtained from *Salmonella typhimurium,*" *J. Biol. Chem.* 258:12947-12951, The American Society of Biological Chemists, Inc. (1983).

Qureshi, N., et al., "Complete Structural Determination of Lipopolysaccharide Obtained from Deep Rough Mutant of *Escherichia coli,*" *J. Biol. Chem.* 263:11971-11976, The American Society for Biochemistry and Molecular Biology, Inc. (1988).

Strittmatter, W., et al., "Nontoxic Lipopolysaccharide from *Rhodopseudomonas sphaeroides* ATCC 17023," *J. Bacteriol.* 155:153-158, American Society for Microbiology (1983).

"The Genetic Improvement of Product Formation," in *Molecular Biology and Biotechnology*, Walker, J.M., and Gingold, E.B., eds., Royal Society of Chemistry, London, Great Britain, pp. 15-20, The Royal Society of Chemistry (1988).

Tsukada, Y., and Perlman, D., "The Fermentation of L-Sorbase by *Gluconobacter melanogenus*. I. General Characteristics of the Fermentation," *Biotechnology and Bioengineering XIV*:799-810, John Wiley & Sons, Inc. (1972).

Yin, G.-L., et al., "Studies on the Production of Vitamin C Precursor 2-Keto-L-Gulonic Acid From L-Sorbase By Fermentation. I. Isolation, Screening and Identification of 2-Keto-L-Gulonic Acid Producing Bacteria," *Acta Microbiologica Sinica* 20:246-251, Weishengwu Xuebao (1980).

Yin, G.-L., et al., "Studies on the Production of Vitamin C Precursor 2-Keto-L-Gulonic Acid From L-Sorbase By Fermentation," *Acta Microbiologica Sinica* 21:185-191, Weishengwu Xuebao (1981).

Zuckerman, S.H., and Qureshi, N., "In Vivo Inhibition of Lipopolysaccharide—Induced Lethality and Tumor Necrosis Factor Synthesis by *Rhodobacter sphaeroides* Diphosphoryl Lipid A Is Dependent on Corticosterone Induction," *Infection and Immunity* 60:2581-2587, American Society for Microbiology (1992).

English Translation of Document AR12, Yin, G.-L., et al., "Studies on the Production of Vitamin C Precursor 2-Keto-L-Gulonic Acid from L-Sorbase by Fermentation. I. Isolation, Screening and Identification of 2-Keto-L-Gulonic Acid Producing Bacteria," *Acta Microbiologica Sinica* 20:246-251, Weishengwu Xuebao (1980).

English Translation of Document AS12, Yin, G.-L., et al., "Studies on Production of Vitamin C Precursor 2-Keto-L-Gulonic Acid From L-Sorbase By Fermentation," *Acta Microbiologica Sinica 21:*185-191, Weishengwu Xuebao (1981).

English Translation of Japanese Patent Publication No. JP 41-159, Mochizuki, K., et al., published Jan. 8, 1966 (Document AN1).

English Translation of Japanese Patent Publication No. JP 41-160, Mochizuki, K., et al., published Jan. 8, 1966 (Document AO1).

English Translation of Japanese Patent Publication No. JP 41-5907, Mochizuki, K., et al., published Mar. 30, 1966 (Document AP1).

Dialog File 351, Accession No. 77-48308Y/27, Derwent WPI English language abstract for U.S.S.R. Patent Publication No. 526,660 (Document AL2).

Dialog File 351, Accession No. 95-155907/21, Derwent WPI English language abstract for Chinese Patent Publication No. CN 1,081,470 A (Document AP3).

Dialog File 347, Accession No. 04958071, JPO & JAPIO English language abstract for Japanese Patent Publication No. JP 7-250671 (Document AM4).

Dialog File 351, Accession No. 4053025, Derwent WPI English language abstract for JP 59-113896 (Document AM2).

Dialog File 351, Accession No. 7580312, Derwent WPI English language abstract for EP 0 276 832 A2 (Document AL3).

Dialog File 351, Accession No. 8924746, Derwent WPI English language abstract for JP 3-294281 (Document AN3).

Dialog File 351, Accession No. 10242604, Derwent WPI English language abstract for JP 7-67673 (Document AL4).

Dialog File 351, Accession No. 10985312, Derwent WPI English language abstract for JP 8-245702 (Document AN4).

* cited by examiner

SEQ ID NO:1

```
   1 GGCAATGGGT CGAAATTCAT AGAATTTTGT GTGAGGTGCG TAGCGGCTCT
  51 GACAGGGGTG CTGCGCGGAG ATCTCTGGTC TCAGGTAGGG CGACAATGGA
 101 GAGGTGTTAG TTGCCCCCTG TATCGCTCTC TGCGTGGCGC ATTGGGTCAT
 151 CCTGCCCGGA CATATGATAT TCCGCTAGAG GATTACTGAT AGTTTCTGCC
 201 TGTCGGGCTT GTCGGGCTTG TCGGGCTTGT CGGGCTTGTC GGGCCTGTCC
 251 CTCTTGTCCC GCCTGTCCTC ACTTTTTCAC AATCAAAAAA TGGGCGAAGC
 301 CCTTCTTGTT CTATAGTTCT TATAGTTCAT ACGAAAATTA CACATAATTA
 351 TCAATAGCTT ATTCGCTTAA AAGGGAGTAA TTGGGCCGCA AAAGGGAGTA
 401 ATTGGGCCGC AAAAGGGAGT AATTGGGCCG CAAAAGGGAG TAATTGGGCC
 451 GATATCGGTT GTTTACATGG GGAGGAATCC CCTTAATCAT TTCTCCCCAT
 501 GGGAAAGACA ACACAAGTGG CCGCAGACCG GGCCTTCGAC CAGACAAAAA
 551 CTGTGCTCCC TGCCGAGGTG GCGAGAGGGG TCTATATGCG CAATCCGCCC
 601 CGCCTGCAGG CGCTCAAGCT CATGCATTTA ATGATAGCCA CTGCGGGCGG
 651 CCGCATGGCT GATGATGTGC GCCATGAAAT GCGGCTGGCC GACATTCGCG
 701 CAATCGACGG CATGAAAAAC CATGACCGTG AGAGCCTGAC CCGCTGTTC
 751 GAGGAGCTAG CCGCTGCGGT GTTGACCCAT GATGACCCTG CAAAGATGAT
 801 CGTGACAGTC GGCGGCTTGG TCGATGAGGC GCGAATAGAC TACCGCCAGG
 851 AGGCAAGCGG CGAACTCCTA GTGACGTGGA CCTTCCGGAG TACATTCCGT
 901 CGTATGGCGG CGGAGTCGAA CCACTGGGCC ATTCTCGACC GTCAAACGGT
 951 ATTCCATCTC GGTAGTAAGT ATTCCGTGCT GCTGTTCCAG CACGTCTCTA
1001 GTCTCGCCAA TCTTGATCGG ATGAGCGCGA AAACCTTTAC GGTCCCCGAG
1051 TTGCGGGCGC TCCTTGAGT GCCCGAGGGA AGATGGTTC GTTGGAACGA
1101 CGTTAACAGA TTTGCTCTCA AACCTGCACT GGATGAGATC AACCATTTAT
1151 CGCGTCTGAC ATTGACGGCA AAGCCGACCA AGATTGGCCG TAGCGTGGCA
1201 AGTGTGACTA TAGGCTGGGA AGTGAAAGAC GACCCAACCG TCGCCAGGCG
1251 CGAGCTGGCG GGTTCCAAGG TCGGTCGAGA TGCTCGTCGC AGAGGGGCAG
1301 CGGAAACGAT AGCCCCCTCC TTCCCAGAAG CGGGCGGGAT CACCTACAGT
1351 CCACGTTGGC TGGAGCTGAA ACGCTCTGCT GGCAGCAACA AGGACAACGA
1401 TCTGATCGCC TCAGACTTCC GGCGTTTCTG TCGGGAGAGA GGCGTGCGTC
1451 TGGACGCTGC AAACATCGAA AAACTGTTTT TAGATTTCTG CGCAAAGGTA
1501 GGGAAGGTTT GAGTTTTGAG GTATTTCACC GCAATAGTGT TAAATGACTT
1551 TCGTGAAACG ATGTGCAATA TAGCGGTAAG ACTATGAAAT ACACGGCTGG
1601 ACAGGCTGCA AAAGCAACGG GTGTGGCGAC CGCAACCATC ACTCGGGCGC
1651 TAAAAAGCGG TAAAATTTCC GGTAAAAAAG ATGAATCTGG GGCATGGGTT
1701 ATAGATCCTG CAGAATTGCA CAGAGTGTTT CCTCCCATTT CAAAGAAATA
1751 CACCGAAACA CCTAACACGC AAGTATATGG TAAGCGTGAT GAAACACATG
1801 AAATGACCTC AGAAATCAGC GCATTAGAGC GTGAAGTTCG ACTTTACGC
1851 GATGCTTTAT CTGATGCCAG GGAGGATCGC GACAAATGGC GCGACATGGC
1901 CGAGCGTCTT TCAATTTCAT CACCGATGAG AGAGGAAGAC CGCCCCCCTC
1951 AAAAACAAAG ATGGTGGAAG ATATTCTGAT CCTGGGCTTC AGGAGCCTTG
```

FIGURE 1A

```
2001  CCTTTACTGG CGGAAAAACG CGATATTGAG GCACAGGCCC GCACTTTAGA
2051  GGCGGAAGCC TATAACGAGT ACCAAAACAC TAGAAGCCAG ATTGAGGAAA
2101   ATAGGGAACG TG
```

FIGURE 1B

SEQ ID NO:2

```
   1 TGGTGAACGC ATTGGCTTGA TGTTTGAGAA AAGCGAAAAG ACCCGGCCAC
  51 AGTTGTGGGT AGAGCGTCGA TATGTGCAAG ACCTGATGCT TGCTGACATC
 101 GAACTCCGTG TCTACCTCGC ATCGTCGCTG TATCAGCCTG CTGCGGATGG
 151 CGGAAAGCCC GCCTATGGTC GTCACGCAGC CCTTAAGGCG ATGCGCGACT
 201 TGGCCCATGC CGATCTGGTG CGTTTCACCA TCGGCCGGAT TACGCAACTG
 251 GAGATGATCC TAGAGCGGTT AACCGAGACA TCTGGTTAAC GCCATAAAGG
 301 CTGCGGCATG AAAATAGGCG GACAATCTGC GCTTGGCCGC CCCCGTTCTC
 351 AGCCGTGCTT GCTCTCTGCC TGCATGGCAC GACGCAGGAT CGCGTTCATA
 401 CGGGTCTGAT ATCCAGACCC GCCCGCCTTG AGCCATGCCA GCACATCGGC
 451 ATCAAGCCGC GCGGTGATCT GCTGCTTGAT CGGGCGATAG AAGCGCCCAC
 501 GCTCGGCGTC TGCCCATTGG GCTTCGGTCA GCTCGGGAAC ATCGTTGGTG
 551 TCGATCTGCT CGGGCGGCAG AGCGTCCAGC CGCGCCAATT TCTTGCGGCG
 601 CTCCTCGGTA AGAGCGGGCA GCGTATCGAA GGTGTATTCA ACCATTGGCA
 651 TATCTCTTCC TTTCCTGCGG TGTAGCGCGG CGAGCCGAAA TGATGCGGAT
 701 CGTCTCGACC GGATCGGGGC CAGCCTCGAT GATCAGGTGG GCAACCAGAA
 751 GGACGGCAGC GCCATAGATC TGCCCAACGG TTTGCCAGCG GTATTCCCCG
 801 CCCTCGATCC TATCCTGAAC CGTCAGGTGC AACGGATCGG CGAACACATG
 851 CACAGCATCC TCGAACCGGA TGCCATGCTT CTTTTCGTTC GTTTCCGCCT
 901 TGGCGGGATC CCAGATAAAC CGCATCTTCA TGGCAGAATT ATAACTACAC
 951 ATTTGTAGTT ATTCAATGGC AAGTCGCAGG TTCAAATCAC GCCCCCAAAC
1001 CGCAACTGTA TTCGTTCTAC TCACGCGCGC TTTTGAATAG AAGCTTGCAT
1051 GATAACACCC GCCGCGTCCT CAACAAAATA AGGCAAATCC GCCGCGCTGG
1101 CGCAATCTGC GCTTTGTCGA TGCAAGGTCT TGTGGTTTCA TACTGCAAGA
1151 GCATGCAAGG AATTGCCCCG GATGAGCACC ACGACGACAC CCACCAAGCC
1201 GGCCTGGAAC AAGGGCCGCG TTGTCGGGAA AAAGCCGCCG CTGACACCTG
1251 ACCAGATTGC CCTGATCCGT CTCATCCTGC GCCAGGAACG GGCGTGGCGG
1301 GATCTGGCTC TGTTCAACGT GGCGATCGAC ACCAGTTTGC GCGGCTCGGA
1351 CCTCGTGCGC CTGCGCGTCT CGGATGTGGC GACCCCAGCT GGTCTGCGTG
1401 AGATCGTCGA GATCCGCCAG AAGAAGACCG AGGCCCGCAA TGTCCGCCCC
1451 GTACAGGCCC GCCTGTCGGA GGGGACACGC GAGAGCCTGC GGGTCTATCT
1501 CGCGGCCTCT GACAAGCCGC TGCACAGCTG GCTGTTCACC GGACAGGGCA
1551 TCCGCTGGTC CCACACCCAC CTTAGCGAGA GCCAGCTGTG GCGCCTGTTC
1601 AAGTCCTGGC TCGAGAAGGC GCGGCTCGAT CCCAGCCTCT ACGGGCTGCA
1651 CTCGCTGCGC CGAACCTTCC CCAGCCACAT CTACCGCGAG ACCGGCAATC
1701 TGCGCGCCGC ACAGCTGCTG CTGGGCCATG CCAGCATCGA GAGCACCAAG
1751 GAGTACATCG GCACCGAGCA AGCCGAGGCC CTCGATATCG CACGGAGGTA
1801 TCACCTCTAA CCCATGGAGA CCTATCTCGA GAAGCGCATC CCCGCCAAGA
1851 ACACAGCACG GTTCTACCGC ATGGCGGTCC TGCCGAACCT GTTCGGGGAA
1901 TGGACGCTGT ATCGAGAATG GGGCCGCATT GGCATCAGCG GCCGCATCCG
1951 GCTCGATTGG TTTGAGAGTG AACAAGATGC CATCGCTGCG ATGCTCGCCA
```

FIGURE 2A

```
2001  TCGAGACCGC CAAGCGTCAG CGCGGGTATT GGCTCGAGCC CATCCAGATT
2051  GACATGTTCC CAGGGGCATA ACAGGCCATC AATGTAAGAG TGCAAGCGGA
2101  GCAAGCAAAA GCCATTTCAC AGTGAGGTGG CAGATGTTCC TGTTTCACAG
2151  TGAAAGCGCT GATGCTGTTT CCACGCCACA GACTGATACG ACCAAAGCAA
2201  CGGGGTCTGC CGCCACAGAC CGGTTCGCCG GCCACCCGCA GAAACGCAGG
2251  TAAAATGGCG ATTTCCGCAA AAAACCGTG CAAATGATGG CAAATCACCA
2301  TCCAGTTTCA TCCTGAAACC CGTCGCTCAA CATGAACGAG CAGGCCATCA
2351  TCCAAGCCCC AGAAACGCGG TGCGGCGACT ACAGATGAGC GATGTTCTGG
2401  CTCATAGGCT GCAAGGCCCT GCAACAGTGA TTTCACCGTG AGATTGCAGG
2451  GTCTTTTGGC TCTCCCGCAA GAGCCACCTC AGGGTGAGCG AGCTAGCCGT
2501  CTAGGTTCAC AGTGAAATCG CTGAGGAGCG TTGCGGGGCT TATGGTTTGG
2551  CTGGTCACGT TGGCCATCGG AATGGAGCAT ACGATGGCTT CTACGCAGTC
2601  GAATCCTGAG GCTTCACGTG GAAAAATAC GCTCCAAAAA AGCCCTGACC
2651  AAATCTTGGA AAAATTGCTT GAAAAGTTTG CTTCTAAAAA ACTGGGAACG
2701  AGATATGCAC GAGATCCCTT ACGAGTGCTG TAGGAGTAAT GCAGTGGACA
2751  AAAACGCCAT TTTTTGCCCC AGTAGGAGTA ATGGAGTGGT TATTTTTTGG
2801  GAGATTTTGC TTCAGTAGGA GTAACGCGTT GGTTAAATTT GCTTGATTGG
2851  CGGTTCAAAT CGACCACCGA GCTGCCGTTG GTCGTATTCG ATCTGCCCCG
2901  CAATTGGGCA CTTGCAGGCC ATCCCCTGA ACTTCTGGCG ATGACCATTT
2951  CGAAGGCAAT GGGTCGAAAT TCATAGAATT TTGTGTGAGG TGCGTAGCGG
3001  CTCTGACAGG GGTGCTGCGC GGAGATCTCT GGTCTCAGGT AGGGCGACAA
3051  TGGAGAGGTG TTAGTTGCCC CCTGTATCGC TCTCTGCGTG GCGCATTGGG
3101  TCATCCTGCC CGGACATATG ATATTCCGCT AGAGGATTAC TGATAGTTTC
3151  TGCCTGTCGG GCTTGTCGGG CTTGTCGGGC TTGTCGGGCT TGTCGGGCCT
3201  GTCCCTCTTG TCCCGCCTGT CCTCACTTTT TCACAATCAA AAAATGGGCG
3251  AAGCCCTTCT TGTTCTATAG TTCTTATAGT TCATACGAAA ATTACACATA
3301  ATTATCAATA GCTTATTCGC TTAAAGGGA GTAATTGGGC CGCAAAAGGG
3351  AGTAATTGGG CCGCAAAAGG GAGTAATTGG GCCGCAAAAG GGAGTAATTG
3401  GGCCGATATC GGTTGTTTAC ATGGGGAGGA ATCCCCTTAA TCATTTCTCC
3451  CCATGGGAAA GACAACACAA GTGGCCGCAG ACCGGGCCTT CGACCAGACA
3501  AAAACTGTGC TCCCTGCCGA GGTGGCGAGA GGGGTCTATA TGCGCAATCC
3551  GCCCCGCCTG CAGGCGCTCA AGCTCATGCA TTTAATGATA GCCACTGCGG
3601  GCGGCCGCAT GGCTGATGAT GTGCGCCATG AAATGCGGCT GGCCGACATT
3651  CGCGCAATCG ACGGCATGAA AAACCATGAC CGTGAGAGCC TGACCCCGCT
3701  GTTCGAGGAG CTAGCCGCTG CGGTGTTGAC CCATGATGAC CCTGCAAAGA
3751  TGATCGTGAC AGTCGGCGGC TTGGTCGATG AGGCGCGAAT AGACTACCGC
3801  CAGGAGGCAA GCGGCGAACT CCTAGTGACG TGGACCTTCC GGAGTACATT
3851  CCGTCGTATG GCGGCGGAGT CGAACCACTG GCCATTCTC GACCGTCAAA
3901  CGGTATTCCA TCTCGGTAGT AAGTATTCCG TGCTGCTGTT CCAGCACGTC
3951  TCTAGTCTCG CCAATCTTGA TCGGATGAGC GCGAAAACCT TTACGGTCCC
4001  CGAGTTGCGG GCGCTCCTTG GAGTGCCCGA GGGAAAGATG GTTCGTTGGA
4051  ACGACGTTAA CAGATTTGCT CTCAAACCTG CACTGGATGA GATCAACCAT
```

FIGURE 2B

```
4101  TTATCGCGTC TGACATTGAC GGCAAAGCCG ACCAAGATTG GCCGTAGCGT
4151  GGCAAGTGTG ACTATAGGCT GGGAAGTGAA AGACGACCCA ACCGTCGCCA
4201  GGCGCGAGCT GGCGGGTTCC AAGGTCGGTC GAGATGCTCG TCGCAGAGGG
4251  GCAGCGGAAA CGATAGCCCC CTCCTTCCCA GAAGCGGGCG GGATCACCTA
4301  CAGTCCACGT TGGCTGGAGC TGAAACGCTC TGCTGGCAGC AACAAGGACA
4351  ACGATCTGAT CGCCTCAGAC TTCCGGCGTT TCTGTCGGGA GAGAGGCGTG
4401  CGTCTGGACG CTGCAAACAT CGAAAAACTG TTTTTAGATT TCTGCGCAAA
4451  GGTAGGGAAG GTTTGAGTTT TGAGGTATTT CACCGCAATA GTGTTAAATG
4501  ACTTTCGTGA AACGATGTGC AATATAGCGG TAAGACTATG AAATACACGG
4551  CTGGACAGGC TGCAAAAGCA ACGGGTGTGG CGACCGCAAC CATCACTCGG
4601  GCGCTAAAAA GCGGTAAAAT TTCCGGTAAA AAGATGAAT CTGGGGCATG
4651  GGTTATAGAT CCTGCAGAAT TGCACAGAGT GTTTCCTCCC ATTTCAAAGA
4701  AATACACCGA ACACCTAAC ACGCAAGTAT ATGGTAAGCG TGATGAAACA
4751  CATGAAATGA CCTCAGAAAT CAGCGCATTA GAGCGTGAAG TTCGGACTTT
4801  ACGCGATGCT TTATCTGATG CCAGGGAGGA TCGCGACAAA TGGCGCGACA
4851  TGGCCGAGCG TCTTTCAATT TCATCACCGA TGAGAGAGGA AGACCGCCCC
4901  CCTCAAAAAC AAAGATGGTG GAAGATATTC TGATCCTGGG CTTCAGGAGC
4951  CTTGCCTTTA AAACCTGAAT CAGCATTCTA GCGATGCTGA TAAGAAGTAA
5001  ATATAGCCAC AATAGAGCGG CCATTTTCCA TTCACATACA GCTCATCATG
5051  TGATCAATAT CAAGTATTGA TATTCATCAA TGGAGAAGAA TTTACATGTA
5101  TCACAGGATC ATCACAGCAT TTGTTTTTGT ATTTCTAAGT GCTAACATAA
5151  CTATCGCTGG CCCTAAAGAA GATTGTACTA TTGCAGTATC TCACCTTGGG
5201  TTTCAGACCG ATAATTACAG CTTTGTCGAA GCCGGTTTTT TTGCCAGAGA
5251  GAGACACGTT TTTGATGGTG TAATAAACTG CTACGTATCT CATGATGGTA
5301  ACATACACAG CATCATCCGG GGCAACACAC CTCTTATGGA AGATGGATAT
5351  TATGGCCCAG AAGTACTGGC GGAAAAACGC GATATTGAGG CACAGGCCCG
5401  CACTTTAGAG GCGGAAGCCT ATAACGAGTA CCAAAACACT AGAAGCCAGA
5451  TTGAGGAAAA TAGGGAACGT GCCCTCGAGG CGCTGCGGCT AGCTAGCAGT
5501  CCTTTTATTA ATAATGGTAG TACAGAAGAA CAGACAATTA TACAGGCCGC
5551  AACTCCGACG GCAGATCCTG TTGTATCTGT ACCCGTGGCA TCTCCAGAAT
5601  CTAAACAAAG TCGAGAGCCG GAACCGGCTG CTGTTCCAGC ATCAGTTTCT
5651  GTTAGAGAGA TGTGGAGCAC GGCTGACAGA TTGACCACCC GTACATGCCC
5701  ATCGACTCGA TGCGGAGCAA CTAGCTGGGT AACAGATGGA ACTAAAGTAA
5751  CAGTTTATGA AGAAAAAGAC GGTTGGTCTA GAATCGGAGA GCTACAGTCT
5801  GCAATGTGCA TAAATGGAAT AAGTGGCGCG GTCGATTCAG GTGAATCTTC
5851  CTGCAATCCC ACCAATGGTA TCGTTAATGG GCAATTCGCA CCCTGGGTTT
5901  TCTCGGATTA TCTTACGATC CAAGAGCCAG AAGCTCCCAT ATCCACCCAA
5951  GAGTGTCGAA ATATGGGGCT CGAGAACTCA GATAATTACC GTATCTATTC
6001  TAGTCAGTTC TGCACTGCCG CTCTCGAAAT GATCAACGAT AGAGTATGCA
6051  ATACATCTGA TTTCAGAGAT TTAGCTTGGT TATCTTCTCC TGAAAGAGGA
6101  CAGGATTACT ACTTCACCTA TTGTGGCGGA TTTCAACCTC AAAACAGATG
6151  GTATTTGAAT GTCAGGACAG GTGAAATCAC CCGCTGATAT TCCACCAAGG
```

FIGURE 2C

```
6201  TGAGTCCTGT AGATCAGACT CTCAAGGAGT AAACGTTTTA ATCCATCTCC
6251  ATGAGATCAA CATAGATAGG TGTTCAGTCC CGGCATCTGG TGGATCGGGT
6301  TTAGGATGAA TCTGTCCGGC TCTTGACATA CCCCCGCGTG AAACCCTGTC
6351  TTTACAAGAG AAAGTCAGCG GCCTCGAAGC CGCTCTAGCC GATGCCCGGG
6401  CCCAACGGGA TGAGTAGAGC GAACAAGCAA AGCGCCTAGC TATGGCTCTG
6451  CCCGTCCCGG AAGCTGCAGC CGCAGAATCC GGAAAAAAGA AAAAATACAT
6501  GGCAGCGATT ATTTGGATAG GACACAATCC TTTTCTATTA ATATACAACA
6551  AGATATGGGC ATGCGCCGCG CGTGATCCTC ATTCGATACA ATCCAAATCC
6601  TGAAAGCTGA CTATGCCCTA CGCATCGCGC ACCATCGGTG CCGTCATTGA
6651  TGACGTGAAC CGCACCTACC TGCTGCCCGC AATCCAACGC CCCTATGTCT
6701  GGTCTGCCGG ACAGGTCGTT GCGCTGTTCG ACTCTCTGTT GAAGGGCTAT
6751  CCGATCAGCA GCTTCATGTT CTGGGCGGTG GACGAGGAGA CCAAGGCAGA
6801  GCTGCGATGC TACAAATTCA TCGAGAATTA TCGGCCCGAA ATGATGAACG
6851  AGCCGACTAG TGCGGACGGG CGGCAGGTCG TCCTTGTGCT CGACGGACAG
6901  CAGCGGATGA CCTCACTGTT GATCGGCTTG CGCGGCACAT TCTCTGAGAA
6951  AGCCAAACAC GCGCGCAACA GCAACGCGGC GGCGTGGTCG GCAAAAACGC
7001  TATATCTAGA CCTGCTTCGG GACCCGGATC CGAAGAACTC CGATGAAGAC
7051  GAAGGCAATG AGTTCGGAAT CACTTACGGT CTCTCTTTCC ATGAACGCCG
7101  CCCGACCAGC AGCCACAGGC ACCACTGGTT CAAGGTGGGA TCGATACTGG
7151  ATTATCCTAC AGACGAGCAG CTGGAGGGGT TGATTGCCAA GGTGAAGACC
7201  GAATTTCATC ATGGTGTATC GGATTGGGAA AAGGGGCTGG CGGAAGACAC
7251  CCTGCGCCGG TTGCACCGCG TCATCTGGAA AGACGAGGGC ATCAACTTTT
7301  TCACTGAACG CGACCAGTCG GTTGATCGGG TGCTGGACAT CTTCGTGCGG
7351  GCCAATGACG GGGGCACGAA ACTGTCGAAG GCAGACCTGC TGATGTCGAT
7401  GATCACGTCA AAATGGTCCA GCGGATCGGC CCGCGAGGAA ATCGGCGGCT
7451  TTGTCGAGCA CATAAACAAA GGTCTCGGTG CGCCGAACAA GATCAGTCGC
7501  GATCTGGTCC TGAAGGCCTG TCTGGTCGTC TGCGATTATG ATGTCGTCTA
7551  TAATGTCAGG AACTTTACAA GCGAGGTCAT CGGCAGGATC GAAAGCAACT
7601  GGGATCGTAT CAAGCAGGCA TTCGAGAACA CGTTCCGCCT GCTGAACAGG
7651  CATGGCATCA CCGGGGATAA CCTCGGCTCT TTGAACGCGG TGCTGCCTCT
7701  GGTCTATTAT ATCTACAACA CGCCGGATTT CGATTTCCGA GGATCGAGCG
7751  AGTTCGAGCG GGTCAATGCC AGCTCCATGC ACCTCTGGTT GGTGAACAGC
7801  CTGCTGGTCA GCGCCTTCGT TGGCCATTCG GATCAGACCA TCACCACCGC
7851  GCGCAATACG ATCCGCGATC ACCTGCGTGT AGGCCGCGAT TTCCCAGTAC
7901  GAAAGCTGTT CGATGCCATG GCGAAGGGGG GACGGCTATC TCAGGTGGAT
7951  GAGCGTACCA TCGAAGAATT GCTGGAAATG CAATATGGCA AGCCCCGGAC
8001  CTTCGTTGCG CTGTCGCTGC TCTATCAGGG CATCGACTGG AACGGATCGA
8051  CCTGGCATGT CGATCATATC ATTCCCCAAG CGGACGCTCA GAAAAATGTG
8101  CTGCGCGGGC GCAATCTGCC CGAGCATCGC ATTCAGGAAA TCTTGGGCGC
8151  GGTTAACAGT TTGGGCAACC TGCAACTTTT GCGCGGAGAT GAGAATATCG
8201  AGAAAGGTGC GCTGCCATTC AGGTCATGGA TTACCGGACG CGCGTTGAT
8251  TTCTACGAGC AGCATATGAT CCCGGCGCAC CTTGAACTGT GCGATGTACT
```

FIGURE 2D

```
8301   GCATCTGCCC GAGTTCGTGC GCGAACGGGA AAAGGTGATC CGGCGCCGTT
8351   TGATGGAGTT GGTCGGAGCA CGACGCGCAT GAATGAGGTC GTCTTGTCAC
8401   GCGAAGAGCT GCGTCAATCT TGTCTCGACC TGCTTGAAAA ACGCGCTGTC
8451   GAACACCCTG CGGGACACCA AGGCAAGCTC GCCGCCCGCT ATGTTGTGCA
8501   CCGCGACGA
```

FIGURE 2E

SEQ ID NO:3

```
   1 TCGCGCGTTT CGGTGATGAC GGTGAAAACC TCTGACACAT GCAGCTCCCG
  51 GAGACGGTCA CAGCTTGTCT GTAAGCGGAT GCCGGGAGCA GACAAGCCCG
 101 TCAGGGCGCG TCAGCGGGTG TTGGCGGGTG TCGGGGCTGG CTTAACTATG
 151 CGGCATCAGA GCAGATTGTA CTGAGAGTGC ACCATATGCG GTGTGAAATA
 201 CCGCACAGAT GCGTAAGGAG AAAATACCGC ATCAGGCGCC ATTCGCCATT
 251 CAGGCTGCGC AACTGTTGGG AAGGGCGATC GGTGCGGGCC TCTTCGCTAT
 301 TACGCCAGCT GGCGAAAGGG GGATGTGCTG CAAGGCGATT AAGTTGGGTA
 351 ACGCCAGGGT TTTCCCAGTC ACGACGTTGT AAAACGACGG CCAGTGAATT
 401 CGGCAATGGG TCGAAATTCA TAGAATTTTG TGTGAGGTGC GTAGCGGCTC
 451 TGACAGGGGT GCTGCGCGGA GATCTCTGGT CTCAGGTAGG GCGACAATGG
 501 AGAGGTGTTA GTTGCCCCCT GTATCGCTCT CTGCGTGGCG CATTGGGTCA
 551 TCCTGCCCGG ACATATGATA TTCCGCTAGA GGATTACTGA TAGTTTCTGC
 601 CTGTCGGGCT TGTCGGGCTT GTCGGGCTTG TCGGGCTTGT CGGGCCTGTC
 651 CCTCTTGTCC CGCCTGTCCT CACTTTTTCA CAATCAAAAA ATGGGCGAAG
 701 CCCTTCTTGT TCTATAGTTC TTATAGTTCA TACGAAAATT ACACATAATT
 751 ATCAATAGCT TATTCGCTTA AAAGGGAGTA ATTGGGCCGC AAAAGGGAGT
 801 AATTGGGCCG CAAAAGGGAG TAATTGGGCC GCAAAAGGGA GTAATTGGGC
 851 CGATATCGGT TGTTTACATG GGAGGAATC CCCTTAATCA TTTCTCCCCA
 901 TGGGAAAGAC AACACAAGTG GCCGCAGACC GGGCCTTCGA CCAGACAAAA
 951 ACTGTGCTCC CTGCCGAGGT GGCGAGAGGG GTCTATATGC GCAATCCGCC
1001 CCGCCTGCAG GCGCTCAAGC TCATGCATTT AATGATAGCC ACTGCGGGCG
1051 GCCGCATGGC TGATGATGTG CGCCATGAAA TGCGGCTGGC CGACATTCGC
1101 GCAATCGACG GCATGAAAAA CCATGACCGT GAGAGCCTGA CCCCGCTGTT
1151 CGAGGAGCTA GCCGCTGCGG TGTTGACCCA TGATGACCCT GCAAAGATGA
1201 TCGTGACAGT CGGCGGCTTG GTCGATGAGG CGCGAATAGA CTACCGCCAG
1251 GAGGCAAGCG CGAACTCCT AGTGACGTGG ACCTTCCGGA GTACATTCCG
1301 TCGTATGGCG GCGGAGTCGA ACCACTGGGC CATTCTCGAC CGTCAAACGG
1351 TATTCCATCT CGGTAGTAAG TATTCCGTGC TGCTGTTCCA GCACGTCTCT
1401 AGTCTCGCCA ATCTTGATCG GATGAGCGCG AAAACCTTTA CGGTCCCCGA
1451 GTTGCGGGCG CTCCTTGGAG TGCCCGAGGG AAAGATGGTT CGTTGGAACG
1501 ACGTTAACAG ATTTGCTCTC AAACCTGCAC TGGATGAGAT CAACCATTTA
1551 TCGCGTCTGA CATTGACGGC AAAGCCGACC AAGATTGGCC GTAGCGTGGC
1601 AAGTGTGACT ATAGGCTGGG AAGTGAAAGA CGACCCAACC GTCGCCAGGC
1651 GCGAGCTGGC GGGTTCCAAG GTCGGTCGAG ATGCTCGTCG CAGAGGGGCA
1701 GCGGAAACGA TAGCCCCCTC CTTCCCAGAA GCGGCGGGA TCACCTACAG
1751 TCCACGTTGG CTGGAGCTGA AACGCTCTGC TGGCAGCAAC AAGGACAACG
1801 ATCTGATCGC CTCAGACTTC CGGCGTTTCT GTCGGGAGAG AGGCGTGCGT
1851 CTGGACGCTG CAAACATCGA AAAACTGTTT TTAGATTTCT GCGCAAAGGT
1901 AGGGAAGGTT TGAGTTTTGA GGTATTTCAC CGCAATAGTG TTAAATGACT
1951 TTCGTGAAAC GATGTGCAAT ATAGCGGTAA GACTATGAAA TACACGGCTG
```

FIGURE 3A

```
2001 GACAGGCTGC AAAAGCAACG GGTGTGGCGA CCGCAACCAT CACTCGGGCG
2051 CTAAAAGCG  GTAAAATTTC CGGTAAAAAA GATGAATCTG GGGCATGGGT
2101 TATAGATCCT GCAGAATTGC ACAGAGTGTT TCCTCCCATT TCAAAGAAAT
2151 ACACCGAAAC ACCTAACACG CAAGTATATG GTAAGCGTGA TGAAACACAT
2201 GAAATGACCT CAGAAATCAG CGCATTAGAG CGTGAAGTTC GGACTTTACG
2251 CGATGCTTTA TCTGATGCCA GGGAGGATCG CGACAAATGG CGCGACATGG
2301 CCGAGCGTCT TTCAATTTCA TCACCGATGA GAGAGGAAGA CCGCCCCCCT
2351 CAAAACAAA  GATGGTGGAA GATATTCTGA TCCTGGGCTT CAGGAGCCTT
2401 GCCTTTACTG GCGGAAAAAC GCGATATTGA GGCACAGGCC CGCACTTTAG
2451 AGGCGGAAGC CTATAACGAG TACCAAAACA CTAGAAGCCA GATTGAGGAA
2501 AATAGGGAAC GTGGGATCCT CTAGAGTCGA CCTGCAGGCA TGCAAGCTTG
2551 GCGTAATCAT GGTCATAGCT GTTTCCTGTG TGAAATTGTT ATCCGCTCAC
2601 AATTCCACAC AACATACGAG CCGGAAGCAT AAAGTGTAAA GCCTGGGGTG
2651 CCTAATGAGT GAGCTAACTC ACATTAATTG CGTTGCGCTC ACTGCCCGCT
2701 TTCCAGTCGG GAAACCTGTC GTGCCAGCTG CATTAATGAA TCGGCCAACG
2751 CGCGGGGAGA GGCGGTTTGC GTATTGGGCG CTCTTCCGCG CTCGGTCTTG
2801 CCTTGCTCGT CGGTGATGTA CTTCACCAGC TCCGCGAAGT CGCTCTTCTT
2851 GATGGAGCGC ATGGGGACGT GCTTGGCAAT CACGCGCACC CCCCGGCCGT
2901 TTTAGCGGCT AAAAAAGTCA TGGCTCTGCC CTCGGGCGGA CCACGCCCAT
2951 CATGACCTTG CCAAGCTCGT CCTGCTTCTC TTCGATCTTC GCCAGCAGGG
3001 CGAGGATCGT GGCATCACCG AACCGCGCCG TGCGCGGGTC GTCGGTGAGC
3051 CAGAGTTTCA GCAGGCCGCC CAGGCGGCCC AGGTCGCCAT TGATGCGGGC
3101 CAGCTCGCGG ACGTGCTCAT AGTCCACGAC GCCCGTGATT TTGTAGCCCT
3151 GGCCGACGGC CAGCAGGTAG GCCGACAGGC TCATGCCGGC CGCCGCCGCC
3201 TTTTCCTCAA TCGCTCTTCG TTCGTCTGGA AGGCAGTACA CCTTGATAGG
3251 TGGGCTGCCC TTCCTGGTTG GCTTGGTTTC ATCAGCCATC CGCTTGCCCT
3301 CATCTGTTAC GCCGGCGGTA GCCGGCCAGC CTCGCAGAGC AGGATTCCCG
3351 TTGAGCACCG CCAGGTGCGA ATAAGGGACA GTGAAGAAGG AACACCCGCT
3401 CGCGGGTGGG CCTACTTCAC CTATCCTGCC CGGCTGACGC CGTTGGATAC
3451 ACCAAGGAAA GTCTACACGA ACCCTTTGGC AAAATCCTGT ATATCGTGCG
3501 AAAAAGGATG GATATACCGA AAAAATCGCT ATAATGACCC CGAAGCAGGG
3551 TTATGCAGCG GAAAAGCTTC CTCGCTCACT GACTCGCTGC GCTCGGTCGT
3601 TCGGCTGCGG CGAGCGGTAT CAGCTCACTC AAAGGCGGTA ATACGGTTAT
3651 CCACAGAATC AGGGGATAAC GCAGGAAAGA ACATGTGAGC AAAAGGCCAG
3701 CAAAAGGCCA GGAACCGTAA AAAGGCCGCG TTGCTGGCGT TTTTCCATAG
3751 GCTCCGCCCC CCTGACGAGC ATCACAAAAA TCGACGCTCA AGTCAGAGGT
3801 GGCGAAACCC GACAGGACTA TAAAGATACC AGGCGTTTCC CCCTGGAAGC
3851 TCCCTCGTGC GCTCTCCTGT TCCGACCCTG CCGCTTACCG GATACCTGTC
3901 CGCCTTTCTC CCTTCGGGAA GCGTGGCGCT TTCTCATAGC TCACGCTGTA
3951 GGTATCTCAG TTCGGTGTAG GTCGTTCGCT CCAAGCTGGG CTGTGTGCAC
4001 GAACCCCCCG TTCAGCCCGA CCGCTGCGCC TTATCCGGTA ACTATCGTCT
4051 TGAGTCCAAC CCGGTAAGAC ACGACTTATC GCCACTGGCA GCAGCCACTG
```

FIGURE 3B

```
4101  GTAACAGGAT TAGCAGAGCG AGGTATGTAG GCGGTGCTAC AGAGTTCTTG
4151  AAGTGGTGGC CTAACTACGG CTACACTAGA AGGACAGTAT TTGGTATCTG
4201  CGCTCTGCTG AAGCCAGTTA CCTTCGGAAA AAGAGTTGGT AGCTCTTGAT
4251  CCGGCAAACA AACCACCGCT GGTAGCGGTG GTTTTTTTGT TTGCAAGCAG
4301  CAGATTACGC GCAGAAAAAA AGGATCTCAA GAAGATCCTT TGATCTTTTC
4351  TACGGGGTCT GACGCTCAGT GGAACGAAAA CTCACGTTAA GGGATTTTGG
4401  TCATGAGATT ATCAAAAAGG ATCTTCACCT AGATCCTTTT GGGGGGGGGG
4451  GGCGCTGAGG TCTGCCTCGT GAAGAAGGTG TTGCTGACTC ATACCAGGCC
4501  TGAATCGCCC CATCATCCAG CCAGAAAGTG AGGGAGCCAC GGTTGATGAG
4551  AGCTTTGTTG TAGGTGGACC AGTTGGTGAT TTTGAACTTT TGCTTTGCCA
4601  CGGAACGGTC TGCGTTGTCG GGAAGATGCG TGATCTGATC CTTCAACTCA
4651  GCAAAAGTTC GATTTATTCA ACAAAGCCGC CGTCCCGTCA AGTCAGCGTA
4701  ATGCTCTGCC AGTGTTACAA CCAATTAACC AATTCTGATT AGAAAAACTC
4751  ATCGAGCATC AAATGAAACT GCAATTTATT CATATCAGGA TTATCAATAC
4801  CATATTTTTG AAAAGCCGT TTCTGTAATG AAGGAGAAAA CTCACCGAGG
4851  CAGTTCCATA GGATGGCAAG ATCCTGGTAT CGGTCTGCGA TTCCGACTCG
4901  TCCAACATCA ATACAACCTA TTAATTTCCC CTCGTCAAAA ATAAGGTTAT
4951  CAAGTGAGAA ATCACCATGA GTGACGACTG AATCCGGTGA GAATGGCAAA
5001  AGCTTATGCA TTTCTTTCCA GACTTGTTCA ACAGGCCAGC CATTACGCTC
5051  GTCATCAAAA TCACTCGCAT CAACCAAACC GTTATTCATT CGTGATTGCG
5101  CCTGAGCGAG ACGAAATACG CGATCGCTGT TAAAAGGACA ATTACAAACA
5151  GGAATCGAAT GCAACCGGCG CAGGAACACT GCCAGCGCAT CAACAATATT
5201  TTCACCTGAA TCAGGATATT CTTCTAATAC CTGGAATGCT GTTTTCCCGG
5251  GGATCGCAGT GGTGAGTAAC CATGCATCAT CAGGAGTACG GATAAAATGC
5301  TTGATGGTCG GAAGAGGCAT AAATTCCGTC AGCCAGTTTA GTCTGACCAT
5351  CTCATCTGTA ACATCATTGG CAACGCTACC TTTGCCATGT TTCAGAAACA
5401  ACTCTGGCGC ATCGGGCTTC CCATACAATC GATAGATTGT CGCACCTGAT
5451  TGCCCGACAT TATCGCGAGC CCATTTATAC CCATATAAAT CAGCATCCAT
5501  GTTGGAATTT AATCGCGGCC TCGAGCAAGA CGTTTCCCGT TGAATATGGC
5551  TCATAACACC CCTTGTATTA CTGTTTATGT AAGCAGACAG TTTTATTGTT
5601  CATGATGATA TATTTTTATC TTGTGCAATG TAACATCAGA GATTTTGAGA
5651  CACAACGTGG CTTTCCCCCC CCCCCCATTA TTGAAGCATT TATCAGGGTT
5701  ATTGTCTCAT GAGCGGATAC ATATTTGAAT GTATTTAGAA AAATAAACAA
5751  ATAGGGGTTC CGCGCACATT TCCCCGAAAA GTGCCACCTG ACGTCTAAGA
5801  AACCATTATT ATCATGACAT TAACCTATAA AAATAGGCGT ATCACGAGGC
5851  CCTTTCGTC
```

FIGURE 3C

SEQ ID NO:4

```
   1  GGCAATGGGT CGAAATTCAT AGAATTTTGT GTGAGGTGCG TAGCGGCTCT
  51  GACAGGGGTG CTGCGCGGAG ATCTCTGGTC TCAGGTAGGG CGACAATGGA
 101  GAGGTGTTAG TTGCCCCCTG TATCGCTCTC TGCGTGGCGC ATTGGGTCAT
 151  CCTGCCCGGA CATATGATAT TCCGCTAGAG GATTACTGAT AGTTTCTGCC
 201  TGTCGGGCTT GTCGGGCTTG TCGGGCTTGT CGGGCTTGTC GGGCCTGTCC
 251  CTCTTGTCCC GCCTGTCCTC ACTTTTTCAC AATCAAAAAA TGGGCGAAGC
 301  CCTTCTTGTT CTATAGTTCT TATAGTTCAT ACGAAAATTA CACATAATTA
 351  TCAATAGCTT ATTCGCTTAA AAGGGAGTAA TTGGGCCGCA AAAGGGAGTA
 401  ATTGGGCCGC AAAAGGGAGT AATTGGGCCG CAAAAGGGAG TAATTGGGCC
 451  GATATCGGTT GTTTACATGG GGAGGAATCC CCTTAATCAT TTCTCCCCAT
 501  GGGAAAGACA ACACAAGTGG CCGCAGACCG GCCTTCGAC CAGACAAAAA
 551  CTGTGCTCCC TGCCGAGGTG GCGAGAGGGG TCTATATGCG CAATCCGCCC
 601  CGCCTGCAGG CGCTCAAGCT CATGCATTTA ATGATAGCCA CTGCGGGCGG
 651  CCGCATGGCT GATGATGTGC GCCATGAAAT GCGGCTGGCC GACATTCGCG
 701  CAATCGACGG CATGAAAAAC CATGACCGTG AGAGCCTGAC CCCGCTGTTC
 751  GAGGAGCTAG CCGCTGCGGT GTTGACCCAT GATGACCCTG CAAAGATGAT
 801  CGTGACAGTC GGCGGCTTGG TCGATGAGGC GCGAATAGAC TACCGCCAGG
 851  AGGCAAGCGG CGAACTCCTA GTGACGTGGA CCTTCCGGAG TACATTCCGT
 901  CGTATGGCGG CGGAGTCGAA CCACTGGGCC ATTCTCGACC GTCAAACGGT
 951  ATTCCATCTC GGTAGTAAGT ATTCCGTGCT GCTGTTCCAG CACGTCTCTA
1001  GTCTCGCCAA TCTTGATCGG ATGAGCGCGA AAACCTTTAC GGTCCCCGAG
1051  TTGCGGGCGC TCCTTGGAGT GCCCGAGGGA AGATGGTTC GTTGGAACGA
1101  CGTTAACAGA TTTGCTCTCA AACCTGCACT GGATGAGATC AACCATTTAT
1151  CGCGTCTGAC ATTGACGGCA AAGCCGACCA AGATTGGCCG TAGCGTGGCA
1201  AGTGTGACTA TAGGCTGGGA AGTGAAAGAC GACCCAACCG TCGCCAGGCG
1251  CGAGCTGGCG GGTTCCAAGG TCGGTCGAGA TGCTCGTCGC AGAGGGGCAG
1301  CGGAAACGAT AGCCCCCTCC TTCCCAGAAG CGGGCGGGAT CACCTACAGT
1351  CCACGTTGGC TGGAGCTGAA ACGCTCTGCT GGCAGCAACA AGGACAACGA
1401  TCTGATCGCC TCAGACTTCC GGCGTTTCTG TCGGGAGAGA GGCGTGCGTC
1451  TGGACGCTGC AAACATCGAA AAACTGTTTT TAGATTTCTG CGCAAAGGTA
1501  GGGAAGGTTT GAGTTTTGAG GTATTTCACC GCAATAGTGT TAAATGACTT
1551  TCGTGAAACG ATGTGCAATA TAGCGGTAAG ACTATGAAAT ACACGGCTGG
1601  ACAGGCTGCA AAAGCAACGG GTGTGGCGAC CGCAACCATC ACTCGGGCGC
1651  TAAAAAGCGG TAAAATTTCC GGTAAAAAAG ATGAATCTGG GCATGGGTT
1701  ATAGATCCTG CAGAATTGCA CAGAGTGTTT CCTCCCATTT CAAAGAAATA
1751  CACCGAAACA CCTAACACGC AAGTATATGG TAAGCGTGAT GAAACACATG
1801  AAATGACCTC AGAAATCAGC GCATTAGAGC GTGAAGTTCG GACTTTACGC
1851  GATGCTTTAT CTGATGCCAG GGAGGATCGC GACAAATGGC GCGACATGGC
1901  CGAGCGTCTT TCAATTTCAT CACCGATGAG AGAGGAAGAC CGCCCCCCTC
1951  AAAAACAAAG ATGGTGGAAG ATATTCTGAT CCTGGGCTTC AGGAGCCTTG
```

FIGURE 4A

```
2001  CCTTTAAAAC CTGAATCAGC ATTCTAGCGA TGCTGATAAG AAGTAAATAT
2051  AGCCACAATA GAGCGGCCAT TTTCCATTCA CATACAGCTC ATCATGTGAT
2101  CAATATCAAG TATTGATATT CATCAATGGA GAAGAATTTA CATGTATCAC
2151  AGGATCATCA CAGCATTTGT TTTTGTATTT CTAAGTGCTA ACATAACTAT
2201  CGCTGGCCCT AAAGAAGATT GTACTATTGC AGTATCTCAC CTTGGGTTTC
2251  AGACCGATAA TTACAGCTTT GTCGAAGCCG GTTTTTTTGC CAGAGAGAGA
2301  CACGTTTTTG ATGGTGTAAT AAACTGCTAC GTATCTCATG ATGGTAACAT
2351  ACACAGCATC ATCCGGGGCA ACACACCTCT TATGGAAGAT GGATATTATG
2401  GCCCAGAAGT ACTGGCGGAA AAACGCGATA TTGAGGCACA GGCCCGCACT
2451  TTAGAGGCGG AAGCCTATAA CGAGTACCAA AACACTAGAA GCCAGATTGA
2501  GGAAAATAGG GAACGTG
```

FIGURE 4B

SEQUENCE LISTING

<160> NUMBER OF SEQ ID NOS: 4

<210> SEQ ID NO 1
<211> LENGTH: 2112
<212> TYPE: DNA
<213> ORGANISM: Artificial Sequence
<220> FEATURE:
<221> NAME/KEY: misc_feature
<223> OTHER INFORMATION: replicon from pADM291

<400> SEQUENCE: 1

```
ggcaatgggt cgaaattcat agaattttgt gtgaggtgcg tagcggctct gacagggtg      60
ctgcgcggag atctctggtc tcaggtaggg cgacaatgga gaggtgttag ttgcccctg     120
tatcgctctc tgcgtggcgc attgggtcat cctgcccgga catatgatat tccgctagag    180
gattactgat agtttctgcc tgtcgggctt gtcgggcttg tcgggcttgt cgggcttgtc    240
gggcctgtcc ctcttgtccc gcctgtcctc acttttttcac aatcaaaaaa tgggcgaagc   300
ccttcttgtt ctatagttct tatagttcat acgaaaatta cacataatta tcaatagctt    360
attcgcttaa aagggagtaa ttgggccgca aagggagta attgggccgc aaaagggagt     420
aattgggccg caaaagggag taattgggcc gatatcggtt gtttacatgg ggaggaatcc    480
ccttaatcat ttctccccat gggaaagaca acacaagtgg ccgcagaccg ggccttcgac    540
cagacaaaaa ctgtgctccc tgccgaggtg gcgagagggg tctatatgcg caatccgccc    600
cgcctgcagg cgctcaagct catgcattta atgatagcca ctgcgggcgg ccgcatggct    660
gatgatgtgc gccatgaaat gcggctggcc gacattcgcg caatcgacgg catgaaaaac    720
catgaccgtg agagcctgac cccgctgttc gaggagctag ccgctgcggt gttgacccat    780
gatgaccctg caaagatgat cgtgacagtc ggcggcttgg tcgatgaggc gcgaatagac    840
taccgccagg aggcaagcgg cgaactccta gtgacgtgga ccttccggag tacattccgt    900
cgtatggcgg cggagtcgaa ccactgggcc attctcgacc gtcaaacggt attccatctc    960
ggtagtaagt attccgtgct gctgttccag cacgtctcta gtctcgccaa tcttgatcgg   1020
atgagcgcga aaacctttac ggtccccgag ttgcgggcgc tccttggagt gcccgaggga   1080
aagatggttc gttggaacga cgttaacaga tttgctctca aacctgcact ggatgagatc   1140
aaccatttat cgcgtctgac attgacggca aagccgacca agattggccg tagcgtggca   1200
agtgtgacta taggctggga agtgaaagac gacccaaccg tcgccaggcg cgagctggcg   1260
ggttccaagg tcggtcgaga tgctcgtcgc agaggggcag cggaaacgat agccccctcc   1320
ttcccagaag cgggcgggat cacctacagt ccacgttggc tggagctgaa acgtctgct   1380
ggcagcaaca aggacaacga tctgatcgcc tcagacttcc ggcgtttctg tcgggagaga   1440
ggcgtgcgtc tggacgctgc aaacatcgaa aaactgtttt tagatttctg cgcaaaggta   1500
gggaaggttt gagttttgag gtatttcacc gcaatagtgt taaatgactt cgtgaaacg    1560
atgtgcaata tagcggtaag actatgaaat acacggctgg acaggctgca aaagcaacgg   1620
gtgtggcgac cgcaaccatc actcgggcgc taaaaagcgg taaaatttcc ggtaaaaaag   1680
atgaatctgg ggcatgggtt atagatcctg cagaattgca cagagtgttt cctcccattt   1740
caaagaaata caccgaaaca cctaacacgc aagtatatgg taagcgtgat gaaacacatg   1800
aaatgacctc agaaatcagc gcattagagc gtgaagttcg gactttacgc gatgctttat   1860
ctgatgccag ggaggatcgc gacaaatggc gcgacatggc cgagcgtctt tcaattcat    1920
caccgatgag agaggaagac cgcccccctc aaaaacaaag atggtggaag atattctgat   1980
cctgggcttc aggagccttg cctttactgg cggaaaaacg cgatattgag gcacaggccc   2040
gcactttaga ggcggaagcc tataacgagt accaaaacac tagaagccag attgaggaaa   2100
ataggggaacg tg                                                      2112
```

<210> SEQ ID NO 2
<211> LENGTH: 8509
<212> TYPE: DNA

<213> ORGANISM: Artificial Sequence
<220> FEATURE:
<221> NAME/KEY: misc_feature
<223> OTHER INFORMATION: pADM291

<400> SEQUENCE: 2

| | |
|---|---|
| tggtgaacgc attggcttga tgtttgagaa aagcgaaaag acccggccac agttgtgggt | 60 |
| agagcgtcga tatgtgcaag acctgatgct tgctgacatc gaactccgtg tctacctcgc | 120 |
| atcgtcgctg tatcagcctg ctgcggatgg cggaaagccc gcctatggtc gtcacgcagc | 180 |
| ccttaaggcg atgcgcgact ggcccatgcc gatctggtg cgtttcacca tcggccggat | 240 |
| tacgcaactg gagatgatcc tagagcggtt aaccgagaca tctggttaac gccataaagg | 300 |
| ctgcggcatg aaaataggcg gacaatctgc gcttggccgc ccccgttctc agccgtgctt | 360 |
| gctctctgcc tgcatggcac gacgcaggat cgcgttcata cgggtctgat atccagaccc | 420 |
| gcccgccttg agccatgcca gcacatcggc atcaagccgc gcggtgatct gctgcttgat | 480 |
| cgggcgatag aagcgcccac gctcggcgtc tgcccattgg gcttcggtca gctcgggaac | 540 |
| atcgttggtg tcgatctgct cgggcggcag agcgtccagc cgcgccaatt tcttgcggcg | 600 |
| ctcctcggta agagcgggca gcgtatcgaa ggtgtattca accattggca tatctcttcc | 660 |
| tttcctgcgg tgtagcgcgg cgagccgaaa tgatgcggat cgtctcgacc ggatcggggc | 720 |
| cagcctcgat gatcaggtgg gcaaccagaa ggacggcagc gccatagatc tgcccaacgg | 780 |
| tttgccagcg gtattccccg ccctcgatcc tatcctgaac cgtcaggtgc aacggatcgg | 840 |
| cgaacacatg cacagcatcc tcgaaccgga tgccatgctt cttttcgttc gtttccgcct | 900 |
| tggcgggatc ccagataaac cgcatcttca tggcagaatt ataactacac atttgtagtt | 960 |
| attcaatggc aagtcgcagg ttcaaatcac gcccccaaac cgcaactgta ttcgttctac | 1020 |
| tcacgcgcgc ttttgaatag aagcttgcat gataacaccc gccgcgtcct caacaaaata | 1080 |
| aggcaaatcc gccgcgctgg cgcaatctgc gctttgtcga tgcaaggtct tgtggtttca | 1140 |
| tactgcaaga gcatgcaagg aattgccccg gatgagcacc acgacgacac ccaccaagcc | 1200 |
| ggcctggaac aagggccgcg ttgtcgggaa aaagccgccg ctgacacctg accagattgc | 1260 |
| cctgatccgt ctcatcctgc gccaggaacg ggcgtggcgg gatctggctc tgttcaacgt | 1320 |
| ggcgatcgac accagtttgc gcggctcgga cctcgtgcgc ctgcgcgtct cggatgtggc | 1380 |
| gaccccagct ggtctgcgtg agatcgtcga gatccgccag aagaagaccg aggcccgcaa | 1440 |
| tgtccgcccc gtacaggccc gcctgtcgga ggggacacgc gagagcctgc gggtctatct | 1500 |
| cgcggcctct gacaagccgc tgcacagctg gctgttcacc ggacagggca tccgctggtc | 1560 |
| ccacacccac cttagcgaga gccagctgtg gcgcctgttc aagtcctggc tcgagaaggc | 1620 |
| gcggctcgat cccagcctct acgggctgca ctcgctgcgc gaaccttcc ccagccacat | 1680 |
| ctaccgcgag accggcaatc tgcgcgccgc acagctgctg ctgggccatg ccagcatcga | 1740 |
| gagcaccaag gagtacatcg gcaccgagca agccgaggcc ctcgatatcg cacggaggta | 1800 |
| tcacctctaa cccatggaga cctatctcga gaagcgcatc cccgccaaga acacagcacg | 1860 |
| gttctaccgc atggcggtcc tgccgaacct gttcgggaa tggacgctgt atcgagaatg | 1920 |
| gggccgcatt ggcatcagcg gccgcatccg gctcgattgg tttgagagtg aacaagatgc | 1980 |
| catcgctgcg atgctcgcca tcgagaccgc caagcgtcag cgcgggtatt ggctcgagcc | 2040 |
| catccagatt gacatgttcc agggggcata acaggccatc aatgtaagag tgcaagcgga | 2100 |
| gcaagcaaaa gccatttcac agtgaggtgg cagatgttcc tgtttcacag tgaaagcgct | 2160 |

```
gatgctgttt ccacgccaca gactgatacg accaaagcaa cggggtctgc cgccacagac    2220
cggttcgccg gccacccgca gaaacgcagg taaaatggcg atttccgcaa aaaaaccgtg    2280
caaatgatgg caaatcacca tccagtttca tcctgaaacc cgtcgctcaa catgaacgag    2340
caggccatca tccaagcccc agaaacgcgg tgcggcgact acagatgagc gatgttctgg    2400
ctcataggct gcaaggccct gcaacagtga tttcaccgtg agattgcagg gtcttttggc    2460
tctcccgcaa gagccacctc agggtgagcg agctagccgt ctaggttcac agtgaaatcg    2520
ctgaggagcg ttgcggggct tatggtttgg ctggtcacgt tggccatcgg aatggagcat    2580
acgatggctt ctacgcagtc gaatcctgag gcttcacgtg ggaaaaatac gctccaaaaa    2640
agccctgacc aaatcttgga aaaattgctt gaaaagtttg cttctaaaaa actgggaacg    2700
agatatgcac gagatccctt acgagtgctg taggagtaat gcagtggaca aaaacgccat    2760
tttttgcccc agtaggagta atggagtggt tatttttttgg gagattttgc ttcagtagga    2820
gtaacgcgtt ggtaaatttt gcttgattgg cggttcaaat cgaccaccga gctgccgttg    2880
gtcgtattcg atctgccccg caattgggca cttgcaggcc atcccccctga acttctggcg    2940 atgaccattt cgaaggcaat gggtcgaaat tcatagaatt ttgtgtgagg tgcgtagcgg    3000
ctctgacagg ggtgctgcgc ggagatctct ggtctcaggt agggcgacaa tggagaggtg    3060
ttagttgccc cctgtatcgc tctctgcgtg gcgcattggg tcatcctgcc cggacatatg    3120
atattccgct agaggattac tgatagtttc tgcctgtcgg gcttgtcggg cttgtcgggc    3180
ttgtcgggct tgtcgggcct gtccctcttg tcccgcctgt cctcactttt tcacaatcaa    3240
aaaatgggcg aagcccttct tgttctatag ttcttatagt tcatacgaaa attacacata    3300
attatcaata gcttattcgc ttaaaaggga gtaattgggc cgcaaaaggg agtaattggg    3360
ccgcaaaagg gagtaattgg gccgcaaaag ggagtaattg ggccgatatc ggttgtttac    3420
atggggagga atcccttaa tcatttctcc ccatgggaaa gacaacacaa gtggccgcag    3480
accgggcctt cgaccagaca aaaactgtgc tccctgccga ggtggcgaga gggtctata    3540 tgcgcaatcc gccccgcctg caggcgctca agctcatgca tttaatgata gccactgcgg    3600
gcggccgcat ggctgatgat gtgcgccatg aaatgcggct ggccgacatt cgcgcaatcg    3660
acggcatgaa aaaccatgac cgtgagagcc tgaccccgct gttcgaggag ctagccgctg    3720
cggtgttgac ccatgatgac cctgcaaaga tgatcgtgac agtcggcggc ttggtcgatg    3780
aggcgcgaat agactaccgc caggaggcaa gcggcgaact cctagtgacg tggaccttcc    3840
ggagtacatt ccgtcgtatg gcggcggagt cgaaccactg ggccattctc gaccgtcaaa    3900
cggtattcca tctcggtagt aagtattccg tgctgctgtt ccagcacgtc tctagtctcg    3960
ccaatcttga tcggatgagc gcgaaaacct ttacggtccc cgagttgcgg gcgctccttg    4020
gagtgcccga gggaaagatg gttcgttgga acgacgttaa cagatttgct ctcaaacctg    4080
cactggatga gatcaaccat ttatcgcgtc tgacattgac ggcaaagccg accaagattg    4140
gccgtagcgt ggcaagtgtg actataggct gggaagtgaa agacgaccca accgtcgcca    4200
ggcgcgagct ggcgggttcc aaggtcggtc gagatgctcg tcgcagaggg gcagcggaaa    4260
cgatagcccc ctccttccca gaagcgggcg ggatcaccta cagtccacgt tggctggagc    4320
tgaaacgctc tgctggcagc aacaaggaca acgatctgat cgcctcagac ttccggcgtt    4380
tctgtcggga gagaggcgtg cgtctggacg ctgcaaacat cgaaaaactg ttttagatt    4440 tctgcgcaaa ggtagggaag gtttgagttt tgaggtattt caccgcaata gtgttaaatg    4500
actttcgtga aacgatgtgc aatatagcgg taagactatg aaatacacgg ctggacaggc    4560
```

```
tgcaaaagca acgggtgtgg cgaccgcaac catcactcgg gcgctaaaaa gcggtaaaat    4620
ttccggtaaa aaagatgaat ctggggcatg ggttatagat cctgcagaat tgcacagagt    4680
gtttcctccc atttcaaaga aatacaccga aacacctaac acgcaagtat atggtaagcg    4740
tgatgaaaca catgaaatga cctcagaaat cagcgcatta gagcgtgaag ttcggacttt    4800
acgcgatgct ttatctgatg ccagggagga tcgcgacaaa tggcgcgaca tggccgagcg    4860
tctttcaatt tcatcaccga tgagagagga agaccgcccc cctcaaaaac aaagatggtg    4920
gaagatattc tgatcctggg cttcaggagc cttgccttta aaacctgaat cagcattcta    4980
gcgatgctga taagaagtaa atatagccac aatagagcgg ccattttcca ttcacataca    5040
gctcatcatg tgatcaatat caagtattga tattcatcaa tggagaagaa tttacatgta    5100
tcacaggatc atcacagcat ttgttttgt atttctaagt gctaacataa ctatcgctgg    5160
ccctaaagaa gattgtacta ttgcagtatc tcaccttggg tttcagaccg ataattacag    5220
ctttgtcgaa gccggttttt tgccagagag agacacgtt tttgatggtg taataaactg    5280
ctacgtatct catgatggta acatacacag catcatccgg ggcaacacac ctcttatgga    5340
agatggatat tatggcccag aagtactggc ggaaaaacgc gatattgagg cacaggcccg    5400
cactttagag gcggaagcct ataacgagta ccaaaacact agaagccaga ttgaggaaaa    5460
tagggaacgt gccctcgagg cgctgcggct agctagcagt cctttattt ataatggtag    5520
tacagaagaa cagacaatta tacaggccgc aactccgacg gcagatcctg ttgtatctgt    5580
acccgtggca tctccagaat ctaaacaaag tcgagaccg gaaccggctg ctgttccagc    5640
atcagtttct gttagagaga tgtggagcac ggctgacaga ttgaccaccc gtacatgccc    5700
atcgactcga tgcggagcaa ctagctgggt aacagatgga actaaagtaa cagtttatga    5760
agaaaaagac ggttggtcta gaatcggaga gctacagtct gcaatgtgca taaatggaat    5820
aagtggcgcg gtcgattcag gtgaatcttc ctgcaatccc accatggta tcgttaatgg    5880
gcaattcgca ccctgggttt tctcggatta tcttacgatc caagagccag aagctcccat    5940
atccacccaa gagtgtcgaa atatggggct cgagaactca gataattacc gtatctattc    6000
tagtcagttc tgcactgccg ctctcgaaat gatcaacgat agagtatgca atacatctga    6060
tttcagagat ttagcttggt tatcttctcc tgaaagagga caggattact acttcaccta    6120
ttgtggcgga tttcaacctc aaaacagatg gtatttgaat gtcaggacag gtgaaatcac    6180
ccgctgatat tccaccaagg tgagtcctgt agatcagact ctcaaggagt aaacgtttta    6240
atccatctcc atgagatcaa catagatagg tgttcagtcc cggcatctgg tggatcgggt    6300
ttaggatgaa tctgtccggc tcttgacata ccccgcgtg aaaccctgtc tttacaagag    6360
aaagtcagcg gcctcgaagc cgctctagcc gatgcccggg cccaacggga tgagtagagc    6420
gaacaagcaa agcgcctagc tatggctctg cccgtcccgg aagctgcagc cgcagaatcc    6480
ggaaaaaaga aaaatacat ggcagcgatt atttggatag gacacaatcc ttttctatta    6540
atatacaaca agatatgggc atgcgccgcg cgtgatcctc attcgataca atccaaatcc    6600
tgaaagctga ctatgcccta cgcatcgcgc accatcggtg ccgtcattga tgacgtgaac    6660
cgcacctacc tgctgcccgc aatccaacgc ccctatgtct ggtctgccgg acaggtcgtt    6720
gcgctgttcg actctctgtt gaagggctat ccgatcagca gcttcatgtt ctgggcggtg    6780
gacgaggaga ccaaggcaga gctgcgatgc tacaaattca tcgagaatta tcggcccgaa    6840
atgatgaacg agccgactag tgcggacggg cggcaggtcg tccttgtgct cgacggacag    6900
```

```
cagcggatga cctcactgtt gatcggcttg cgcggcacat tctctgagaa agccaaacac    6960
gcgcgcaaca gcaacgcggc ggcgtggtcg gcaaaaacgc tatatctaga cctgcttcgg    7020
gacccggatc cgaagaactc cgatgaagac gaaggcaatg agttcggaat cacttacggt    7080
ctctctttcc atgaacgccg cccgaccagc agccacaggc accactggtt caaggtggga    7140
tcgatactgg attatcctac agacgagcag ctggagggt tgattgccaa ggtgaagacc     7200
gaatttcatc atggtgtatc ggattgggaa aaggggctgg cggaagacac cctgcgccgg    7260
ttgcaccgcg tcatctggaa agacgagggc atcaactttt tcactgaacg cgaccagtcg    7320
gttgatcggg tgctggacat cttcgtgcgg gccaatgacg ggggcacgaa actgtcgaag    7380
gcagacctgc tgatgtcgat gatcacgtca aaatggtcca gcggatcggc ccgcgaggaa    7440
atcggcggct tgtcgagca cataaacaaa ggtctcggtg cgccgaacaa gatcagtcgc     7500
gatctggtcc tgaaggcctg tctggtcgtc tgcgattatg atgtcgtcta taatgtcagg    7560
aactttacaa gcgaggtcat cggcaggatc gaaagcaact gggatcgtat caagcaggca    7620
ttcgagaaca cgttccgcct gctgaacagg catggcatca ccggggataa cctcggctct    7680
ttgaacgcgg tgctgcctct ggtctattat atctacaaca cgccggattt cgatttccga    7740
ggatcgagcg agttcgagcg ggtcaatgcc agctccatgc acctctggtt ggtgaacagc    7800
ctgctggtca cgcgccttcg tggccattcg gatcagacca tcaccaccgc gcgcaatacg    7860
atccgcgatc acctgcgtgt aggccgcgat ttcccagtac gaaagctgtt cgatgccatg    7920
gcgaaggggg gacggctatc tcaggtggat gagcgtacca tcgaagaatt gctggaaatg    7980
caatatggca gccccggac cttcgttgcg ctgtcgctgc tctatcaggg catcgactgg      8040
aacggatcga cctggcatgt cgatcatatc attccccaag cggacgctca gaaaaatgtg    8100
ctgcgcgggc gcaatctgcc cgagcatcgc attcaggaaa tcttgggcgc ggttaacagt    8160
ttgggcaacc tgcaacttt gcgcggagat gagaatatcg agaaaggtgc gctgccattc      8220
aggtcatgga ttaccggacg gcgcgttgat ttctacgagc agcatatgat cccggcgcac    8280
cttgaactgt gcgatgtact gcatctgccc gagttcgtgc gcgaacggga aaaggtgatc    8340
cggcgccgtt tgatggagtt ggtcggagca cgacgcgcat gaatgaggtc gtcttgtcac    8400
gcgaagagct gcgtcaatct tgtctcgacc tgcttgaaaa acgcgctgtc gaacaccctg    8460
cgggacacca aggcaagctc gccgcccgct atgttgtgca ccgcgacga                8509

<210> SEQ ID NO 3
<211> LENGTH: 5859
<212> TYPE: DNA
<213> ORGANISM: Artificial Sequence
<220> FEATURE:
<221> NAME/KEY: misc_feature
<223> OTHER INFORMATION: pADM291-4DS

<400> SEQUENCE: 3
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120 ttggcgggtg tcgggctgg cttaactatg cggcatcaga gcagattgta ctgagagtgc       180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt cggcaatggg tcgaaattca      420
```

-continued

```
tagaattttg tgtgaggtgc gtagcggctc tgacagggt gctgcgcgga gatctctggt      480
ctcaggtagg gcgacaatgg agaggtgtta gttgccccct gtatcgctct ctgcgtggcg      540
cattgggtca tcctgcccgg acatatgata ttccgctaga ggattactga tagtttctgc      600
ctgtcgggct tgtcgggctt gtcgggcttg tcgggcttgt cgggcctgtc cctcttgtcc      660
cgcctgtcct cacttttca caatcaaaaa atgggcgaag cccttcttgt tctatagttc      720
ttatagttca tacgaaaatt acacataatt atcaatagct tattcgctta aaagggagta      780
attgggccgc aaaagggagt aattgggccg caaagggag taattgggcc gcaaagggga      840
gtaattgggc cgatatcggt tgtttacatg gggaggaatc cccttaatca tttctcccca      900
tgggaaagac aacacaagtg gccgcagacc gggccttcga ccagacaaaa actgtgctcc      960
ctgccgaggt ggcgagaggg gtctatatgc gcaatccgcc ccgcctgcag gcgctcaagc     1020
tcatgcattt aatgatagcc actgcgggcg gccgcatggc tgatgatgtg cgccatgaaa     1080
tgcggctggc cgacattcgc gcaatcgacg gcatgaaaaa ccatgaccgt gagagcctga     1140
ccccgctgtt cgaggagcta gccgctgcgg tgttgaccca tgatgaccct gcaaagatga     1200
tcgtgacagt cggcggcttg tcgatgagg cgcgaataga ctaccgccag gaggcaagcg     1260
gcgaactcct agtgacgtgg accttccgga gtacattccg tcgtatggcg gcggagtcga     1320
accactgggc cattctcgac cgtcaaacgg tattccatct cggtagtaag tattccgtgc     1380
tgctgttcca gcacgtctct agtctcgcca atcttgatcg gatgagcgcg aaaaccttta     1440
cggtccccga gttgcgggcg ctccttggag tgcccgaggg aaagatggtt cgttggaacg     1500
acgttaacag atttgctctc aaacctgcac tggatgagat caaccattta tcgcgtctga     1560
cattgacggc aaagccgacc aagattggcc gtagcgtggc aagtgtgact ataggctggg     1620
aagtgaaaga cgacccaacc gtcgccaggc gcgagctggc gggttccaag gtcggtcgag     1680
atgctcgtcg cagaggggca gcggaaacga tagcccccctc cttcccagaa gcgggcggga     1740
tcacctacag tccacgttgg ctggagctga aacgctctgc tggcagcaac aaggacaacg     1800
atctgatcgc ctcagacttc cggcgtttct gtcgggagag aggcgtgcgt ctggacgctg     1860
caaacatcga aaaactgttt ttagatttct gcgcaaaggt agggaaggtt tgagttttga     1920
ggtatttcac cgcaatagtg ttaaatgact ttcgtgaaac gatgtgcaat atagcggtaa     1980
gactatgaaa tacacggctg acaggctgc aaaagcaacg ggtgtggcga ccgcaaccat     2040
cactcgggcg ctaaaaagcg gtaaaatttc cggtaaaaaa gatgaatctg gggcatgggt     2100
tatagatcct gcagaattgc acagagtgtt tcctcccatt tcaaagaaat acaccgaaac     2160
acctaacacg caagtatatg gtaagcgtga tgaaacacat gaaatgacct cagaaatcag     2220
cgcattagag cgtgaagttc ggactttacg cgatgctttta tctgatgcca gggaggatcg     2280
cgacaaatgg cgcgacatgg ccgagcgtct ttcaatttca tcaccgatga gagaggaaga     2340
ccgccccct caaaaacaaa gatggtggaa gatattctga tcctgggctt caggagcctt     2400
gcctttactg gcggaaaaac gcgatattga ggcacaggcc cgcactttag aggcggaagc     2460
ctataacgag taccaaaaca ctagaagcca gattgaggaa aatagggaac gtgggatcct     2520
ctagagtcga cctgcaggca tgcaagcttg gcgtaatcat ggtcatagct gtttcctgtg     2580
tgaaattgtt atccgctcac aattccacac aacatacgag ccggaagcat aaagtgtaaa     2640
gcctggggtg cctaatgagt gagctaactc acattaattg cgttgcgctc actgcccgct     2700
ttccagtcgg gaaacctgtc gtgccagctg cattaatgaa tcggccaacg cgcgggggaga     2760
ggcggtttgc gtattgggcg ctcttccgcg ctcggtcttg ccttgctcgt cggtgatgta     2820
```

```
cttcaccagc tccgcgaagt cgctcttctt gatggagcgc atggggacgt gcttggcaat    2880
cacgcgcacc ccccggccgt tttagcggct aaaaaagtca tggctctgcc ctcgggcgga    2940
ccacgcccat catgaccttg ccaagctcgt cctgcttctc ttcgatcttc gccagcaggg    3000
cgaggatcgt ggcatcaccg aaccgcgccg tgcgcgggtc gtcggtgagc cagagtttca    3060
gcaggccgcc caggcggccc aggtcgccat tgatgcgggc cagctcgcgg acgtgctcat    3120
agtccacgac gcccgtgatt ttgtagccct ggccgacggc cagcaggtag gccgacaggc    3180
tcatgccggc cgccgccgcc ttttcctcaa tcgctcttcg ttcgtctgga aggcagtaca    3240
ccttgatagg tgggctgccc ttcctggttg gcttggtttc atcagccatc cgcttgccct    3300
catctgttac gccggcggta gccggccagc ctcgcagagc aggattcccg ttgagcaccg    3360
ccaggtgcga ataagggaca gtgaagaagg aacacccgct cgcgggtggg cctacttcac    3420
ctatcctgcc cggctgacgc cgttggatac accaaggaaa gtctacacga acccttttggc   3480 aaaatcctgt atatcgtgcg aaaaggatg gatataccga aaaaatcgct ataatgaccc     3540
cgaagcaggg ttatgcagcg gaaaagcttc ctcgctcact gactcgctgc gctcggtcgt    3600
tcggctgcgg cgagcggtat cagctcactc aaaggcggta atacggttat ccacagaatc    3660
aggggataac gcaggaaaga acatgtgagc aaaaggccag caaaaggcca ggaaccgtaa    3720
aaaggccgcg ttgctggcgt ttttccatag gctccgcccc cctgacgagc atcacaaaaa    3780
tcgacgctca agtcagaggt ggcgaaaccc gacaggacta taaagatacc aggcgtttcc    3840
ccctggaagc tccctcgtgc gctctcctgt tccgaccctg ccgcttaccg gatacctgtc    3900
cgcctttctc ccttcgggaa gcgtggcgct ttctcatagc tcacgctgta ggtatctcag    3960
ttcggtgtag gtcgttcgct ccaagctggg ctgtgtgcac gaaccccccg ttcagcccga    4020
ccgctgcgcc ttatccggta actatcgtct tgagtccaac ccggtaagac acgacttatc    4080
gccactggca gcagccactg gtaacaggat tagcagagcg aggtatgtag gcggtgctac    4140
agagttcttg aagtggtggc ctaactacgg ctacactaga aggacagtat ttggtatctg    4200
cgctctgctg aagccagtta ccttcggaaa aagagttggt agctcttgat ccggcaaaca    4260
aaccaccgct ggtagcggtg gtttttttgt ttgcaagcag cagattacgc gcagaaaaaa    4320
aggatctcaa gaagatcctt tgatctttc tacgggtct gacgctcagt ggaacgaaaa     4380
ctcacgttaa gggattttgg tcatgagatt atcaaaaagg atcttcacct agatcctttt    4440 ggggggggggg ggcgctgagg tctgcctcgt gaagaaggtg ttgctgactc ataccaggcc   4500
tgaatcgccc catcatccag ccagaaagtg agggagccac ggttgatgag agctttgttg    4560
taggtggacc agttggtgat tttgaacttt tgctttgcca cggaacggtc tgcgttgtcg    4620
ggaagatgcg tgatctgatc cttcaactca gcaaaagttc gatttattca acaaagccgc    4680
cgtcccgtca gtcagcgta atgctctgcc agtgttacaa ccaattaacc aattctgatt    4740
agaaaaactc atcgagcatc aaatgaaact gcaatttatt catatcagga ttatcaatac    4800 catattttg aaaagccgt ttctgtaatg aaggagaaaa ctcaccgagg cagttccata     4860
ggatggcaag atcctggtat cggtctgcga ttccgactcg tccaacatca atacaaccta    4920
ttaatttccc ctcgtcaaaa ataaggttat caagtgagaa atcaccatga gtgacgactg    4980
aatccggtga gaatggcaaa agcttatgca tttctttcca gacttgttca acaggccagc    5040
cattacgctc gtcatcaaaa tcactcgcat caaccaaacc gttattcatt cgtgattgcg    5100
cctgagcgag acgaaatacg cgatcgctgt taaaaggaca attacaaaca ggaatcgaat    5160
```

-continued

```
gcaaccggcg caggaacact gccagcgcat caacaatatt ttcacctgaa tcaggatatt      5220
cttctaatac ctggaatgct gttttcccgg ggatcgcagt ggtgagtaac catgcatcat      5280
caggagtacg gataaaatgc ttgatggtcg gaagaggcat aaattccgtc agccagttta      5340
gtctgaccat ctcatctgta acatcattgg caacgctacc tttgccatgt ttcagaaaca      5400
actctggcgc atcgggcttc ccatacaatc gatagattgt cgcacctgat tgcccgacat      5460
tatcgcgagc ccatttatac ccatataaat cagcatccat gttggaattt aatcgcggcc      5520
tcgagcaaga cgtttcccgt tgaatatggc tcataacacc ccttgtatta ctgtttatgt      5580
aagcagacag ttttattgtt catgatgata tatttttatc ttgtgcaatg taacatcaga      5640
gattttgaga cacaacgtgg ctttcccccc cccccatta ttgaagcatt tatcagggtt       5700
attgtctcat gagcggatac atatttgaat gtatttagaa aaataaacaa ataggggttc      5760
cgcgcacatt tccccgaaaa gtgccacctg acgtctaaga aaccattatt atcatgacat      5820
taacctataa aataggcgt atcacgaggc cctttcgtc                              5859
```

<210> SEQ ID NO 4
<211> LENGTH: 2517
<212> TYPE: DNA
<213> ORGANISM: Artificial Sequence
<220> FEATURE:
<221> NAME/KEY: misc_feature
<223> OTHER INFORMATION: Ketogulonigenium part of pADM291-4

<400> SEQUENCE: 4

```
ggcaatgggt cgaaattcat agaattttgt gtgaggtgcg tagcggctct gacagggtg        60 ctgcgcggag atctctggtc tcaggtaggg cgacaatgga gaggtgttag ttgccccctg      120
tatcgctctc tgcgtggcgc attgggtcat cctgcccgga catatgatat tccgctagag      180
gattactgat agtttctgcc tgtcgggctt gtcgggcttg tcgggcttgt cgggcttgtc      240
gggcctgtcc ctcttgtccc gcctgtcctc actttttcac aatcaaaaaa tgggcgaagc      300
ccttcttgtt ctatagttct tatagttcat acgaaaatta cacataatta tcaatagctt      360
attcgcttaa aagggagtaa ttgggccgca aagggagta attgggccgc aaagggagt       420 aattgggccg caaagggag taattgggcc gatatcggtt gtttacatgg ggaggaatcc       480
ccttaatcat ttctccccat gggaaagaca acacaagtgg ccgcagaccg ggccttcgac      540
cagacaaaaa ctgtgctccc tgccgaggtg gcgagagggg tctatatgcg caatccgccc      600
cgcctgcagg cgctcaagct catgcattta atgatagcca ctgcgggcgg ccgcatggct      660
gatgatgtgc gccatgaaat gcggctggcc gacattcgcg caatcgacgg catgaaaaac      720
catgaccgtg agagcctgac cccgctgttc gaggagctag ccgctgcggt gttgaccat       780 gatgaccctg caaagatgat cgtgacagtc ggcggcttgg tcgatgaggc gcgaatagac      840
taccgccagg aggcaagcgg cgaactccta gtgacgtgga ccttccggag tacattccgt      900
cgtatggcgg cggagtcgaa ccactgggcc attctcgacc gtcaaacggt attccatctc      960
ggtagtaagt attccgtgct gctgttccag cacgtctcta gtctcgccaa tcttgatcgg     1020
atgagcgcga aaacctttac ggtccccgag ttgcgggcgc tccttggagt gcccgaggga    1080
aagatggttc gttggaacga cgttaacaga tttgctctca aacctgcact ggatgagatc     1140
aaccatttat cgcgtctgac attgacgcga agccgacca gattggccg tagcgtggca      1200 agtgtgacta ggctgggga agtgaaagac gacccaaccg tcgccaggcg cgagctggcg      1260
ggttccaagg tcggtcgaga tgctcgtcgc agaggggcag cggaaacgat agccccctcc     1320
```

-continued

```
ttcccagaag cgggcgggat cacctacagt ccacgttggc tggagctgaa acgctctgct    1380
ggcagcaaca aggacaacga tctgatcgcc tcagacttcc ggcgtttctg tcgggagaga    1440
ggcgtgcgtc tggacgctgc aaacatcgaa aaactgtttt tagatttctg cgcaaaggta    1500
gggaaggttt gagttttgag gtatttcacc gcaatagtgt taaatgactt tcgtgaaacg    1560
atgtgcaata tagcggtaag actatgaaat acacggctgg acaggctgca aaagcaacgg    1620
gtgtggcgac cgcaaccatc actcgggcgc taaaaagcgg taaaatttcc ggtaaaaaag    1680
atgaatctgg ggcatgggtt atagatcctg cagaattgca cagagtgttt cctcccattt    1740
caaagaaata caccgaaaca cctaacacgc aagtatatgg taagcgtgat gaaacacatg    1800
aaatgacctc agaaatcagc gcattagagc gtgaagttcg gactttacgc gatgctttat    1860
ctgatgccag ggaggatcgc gacaaatggc gcgacatggc cgagcgtctt tcaatttcat    1920
caccgatgag agaggaagac cgcccccctc aaaaacaaag atggtggaag atattctgat    1980
cctgggcttc aggagccttg cctttaaaac ctgaatcagc attctagcga tgctgataag    2040
aagtaaatat agccacaata gagcggccat tttccattca catacagctc atcatgtgat    2100
caatatcaag tattgatatt catcaatgga gaagaattta catgtatcac aggatcatca    2160
cagcatttgt ttttgtattt ctaagtgcta acataactat cgctggccct aaagaagatt    2220
gtactattgc agtatctcac cttgggtttc agaccgataa ttacagcttt gtcgaagccg    2280
gtttttttgc cagagagaga cacgtttttg atggtgtaat aaactgctac gtatctcatg    2340
atggtaacat acacagcatc atccgggggca acacacctct tatggaagat ggatattatg    2400
gcccagaagt actggcggaa aaacgcgata ttgaggcaca ggcccgcact ttagaggcgg    2460
aagcctataa cgagtaccaa aacactagaa gccagattga ggaaaatagg gaacgtg     2517
```

KETOGULONIGENIUM SHUTTLE VECTORS

CROSS-REFERENCE TO RELATED APPLICATIONS

This application claims the benefit of U.S. Provisional Application No. 60/194,625, filed Apr. 5, 2000, the content of which is incorporated herein by reference.

BACKGROUND OF THE INVENTION

1. Field of the Invention

The present invention relates, in general, to vectors comprising a *Ketogulonigenium* replicon. More specifically, the present invention relates to vectors comprising a *Ketogulonigenium* replicon found on the endogenous plasmid contained in Deposit No. NRRL B-30035.

2. Background Information

The exploitation of microorganisms to synthesize vitamin C or its chemical pathway intermediates has both economic and ecological advantages. One key intermediate in vitamin C synthesis is 2-keto-L-gulonic acid (2-KLG), which is easily converted chemically to L-ascorbic acid (vitamin C) by esterification followed by lactonization (Delic, V. et al., "Microbial reactions for the synthesis of vitamin C (L-ascorbic acid," in *Biotechnology of Vitamins, Pigments and Growth Factors*, Vandamme, E. J., ed., Elsevier Applied Science (London & New York) pp. 299–336 (1989)). Members of a number of bacterial genera have been identified that produce 2-KLG from the oxidation of sorbitol. Such 2-KLG producing genera include the acidogenic, alpha-proteobacteria *Gluconobacter* and *Acetobacter*, the gamma-proteobacteria *Pseudomonas, Escherichia, Klebsiella, Serratia* and *Xanthmonas*, the Gram positive *Bacillus, Micrococcus* and the unofficial genus *Pseudogluconobacter* (Imai, K. et al., U.S. Pat. No. 4,933,289 (1990), Sugisawa, H. et al., "Microbial production of 2-keto-L-gulonic acid from L-sorbose and D-sorbitol by *Gluconobacter melanogenus*," *Agric. Biol. Chem.* 54:1201–1209 (1990), Yin, G. et al., U.S. Pat. No. 4,935,359 (1990) and Nogami, I. et al., U.S. Pat. No. 5,474,924 (1995)).

To aid in increasing the yield of bacterial products, attempts have been made to exploit endogenous plasmids within microorganism strains. For example, shuttle vectors derived from endogenous plasmids have been utilized in an attempt increase production of bacterially generated compounds in *Gluconobacter* and *Acetobacter* (Beppu, T. et al., U.S. Pat. No. 5,580,782 (1996), Fujiwara, A. et al., U.S. Pat. No. 5,399,496 (1995), Tonouchi et al, U.S. Pat. No. 6,127,174 (2000), Hoshino, T. et al., U.S. Pat. No. 6,127,156, (2000)).

SUMMARY OF THE INVENTION

The present invention provides an isolated or purified nucleic acid molecule comprising a polynucleotide having a nucleotide sequence at least 95% identical to a nucleotide sequence of a *Ketogulonigenium* plasmid replicon found on the endogenous plasmid contained in Deposit No. NRRL B-30035 (Deposited Jul. 21, 1998, Agriculture Research Culture Collection (NRRL), 1815 N. University Street, Peoria, Ill. 61604, U.S.A.). The invention further provides host cells transformed with the vector of the present invention. The invention also provides a method of producing polypeptides and/or antisense transcripts by culturing host cells transformed with the vector of the present invention.

Further advantages of the present invention will be clear from the description that follows.

BRIEF DESCRIPTION OF THE DRAWINGS

FIG. 1 shows the nucleotide (SEQ ID NO:1) sequence of a replicon of the endogenous plasmid contained in *Ketogulonigenium* strain NRRL Deposit No. B-30035. The nucleotide has a sequence of about 2112 nucleic acid residues.

FIG. 2 shows the nucleotide (SEQ ID NO:2) sequence of the endogenous plasmid determined by sequencing of the endogenous plasmid contained in NRRL Deposit No. B-30035. The nucleotide has a sequence of about 8509 nucleic acid residues.

FIG. 3 shows the nucleotide (SEQ ID NO:3) sequence of a shuttle vector plasmid contained in NRRL Deposit No. B-30434 (Deposited Mar. 27, 2001, Agriculture Research Culture Collection (NRRL), 1815 N. University Street, Peoria, Ill. 61604, U.S.A.). The nucleotide has a sequence of about 5859 nucleic acid residues.

FIG. 4 shows the nucleotide (SEQ ID NO:4) sequence comprising a region that supports plasmid vector replication in *Ketogulonigenium* host species. The nucleotide has a sequence of about 2517 nucleic acid residues.

DETAILED DESCRIPTION OF THE INVENTION

Unless otherwise indicated, all nucleotide sequences determined by sequencing a DNA molecule herein were determined using an automated DNA sequencer (such as the ABI Prism 3700). Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule.

Unless otherwise indicated, each "nucleotide sequence" set forth herein is presented as a sequence of deoxyribonucleotides (abbreviated A, G , C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence in is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxynucleotide A, G or C of SEQ ID NO:1 has been replaced by the corresponding ribonucleotide A, G or C, and each deoxynucleotide T has been replaced by a ribonucleotide U.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

In another aspect, the invention provides an isolated nucleic acid molecule comprising a polynucleotide which hybridizes under stringent hybridization conditions to a portion of the polynucleotide in a nucleic acid molecule of the invention described above, for instance, in the endogenous plasmids contained in NRRL Deposit No. B-30035. By "stringent hybridization conditions" is intended overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 µg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers.

Of course, polynucleotides hybridizing to a larger portion of the reference polynucleotide (e.g., the deposited endogenous plasmid), for instance, a portion 50–750 nt in length, or even to the entire length of the reference polynucleotide, also useful as probes according to the present invention, as are polynucleotides corresponding to most, if not all, of the nucleotide sequence of the deposited DNA or the nucleotide sequence as shown in FIG. 1 (SEQ ID NO:1). By a portion of a polynucleotide of "at least 20 nt in length," for example, is intended 20 or more contiguous nucleotides from the nucleotide sequence of the reference polynucleotide, (e.g., the deposited DNA or the nucleotide sequence as shown in FIG. 1 (SEQ ID NO:1)). As indicated, such portions are useful diagnostically either as a probe according to conventional DNA hybridization techniques or as primers for amplification of a target sequence by the polymerase chain reaction (PCR), as described, for instance, in Molecular Cloning, A Laboratory Manual, 2nd. edition, edited by Sambrook, J., Fritsch, E. F. and Maniatis, T., (1989), Cold Spring Harbor Laboratory Press, the entire disclosure of which is hereby incorporated herein by reference.

By a polynucleotide having a nucleotide sequence at least, for example, 95% "identical" to a reference nucleotide sequence is intended that the nucleotide sequence of the polynucleotide is identical to the reference sequence except that the polynucleotide sequence may include up to five point mutations per each 100 nucleotides of the reference nucleotide sequence encoding the pyruvate carboxylase polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As a practical matter, whether any particular nucleic acid molecule is at least 90%, 95%, 97%, 98% or 99% identical to, for instance, the nucleotide sequence shown in FIG. 1 or to the nucleotide sequence of the deposited endogenous plasmid can be determined conventionally using known computer programs such as the FastA program. FastA does a Pearson and Lipman search for similarity between a query sequence and a group of sequences of the same type nucleic acid. Professor William Pearson of the University of Virginia Department of Biochemistry wrote the FASTA program family (FastA, TFastA, FastX, TFastX and SSearch). In collaboration with Dr. Pearson, the programs were modified and documented for distribution with GCG Version 6.1 by Mary Schultz and Irv Edelman, and for Versions 8 through 10 by Sue Olson.

The present invention provides an isolated or purified vector comprising a nucleic acid molecule comprising a nucleotide sequence of a *Ketogulonigenium* replicon found on the endogenous plasmid contained in Deposit No. NRRL B-30035 (ADM 291-19), pADM291, and at least one exogenous nucleotide sequence. In an additional embodiment of the invention, the *Ketogulonigenium* replicon comprises the nucleotide sequence in SEQ ID NO:1.

As used herein, an exogenous nucleotide sequence is a nucleotide sequence which is not present in the native or wild type endogenous plasmid contained in Deposit No. NRRL B-30035. However, an exogenous nucleotide sequence also includes a sequence endogenous to the plasmid contained in Deposit No. NRRL B-30035, but mutated or non-natively regulated.

*Ketogulonigenium* (Ke.to.gu.lo.ni.gen'.i.um. M. L. n. *acidum ketogulonicum* ketogulonic acid; Gr. v. gennaio to produce; M. L. n. *ketogulonigenium* ketogulonic acid producing) is gram negative, facultatively anaerobic, motile or non-motile, has ovoid to rod-shaped cells, 0.8–1.3 µm long, 0.5–0.7 µm in diameter, with tapered ends, occurring as single cells, pairs and occasionally short chains. Some strains form elongated cells (up to 30 µm in length) on TSB. Flagella and fimbrae have been observed. Colonies are tan colored, smooth, circular, entire, raised to convex, 1–2 mm in diameter with a diffusable brown pigment after 48 hrs incubation. Oxidase and catalase reactions are positive. Optimum temperature range is 27 to 31° C., optimum pH range is 7.2 to 8.5 and optimum $Na^+$ concentration is 117–459 mM. Chemoorganotrophic. Carbon sources utilized include arabinose, cellobiose, fructose, glucose, glycerol, inositol, lactose, maltose, mannitol, mannose, rhamnose, sorbitol, sorbose, sucrose, trehalose, pyruvate and succinate. Favored carbon sources are inositol, mannitol, glycerol, sorbitol, lactose and arabinose. All strains examined produce 2-keto-L-gulonic acid from L-sorbose. Major cellular fatty acids are 16:0 and 18:1 ω7c/ω9t/ω12t and the mol % DNA G+C is 52.1 to 54.0 percent. Small subunit rDNA sequence analysis place this genus in the alpha subgroup of the Proteobacteria. All strains isolated in the present study group originated in soil. DNA reassociation studies divide the genus into two species. *K. vulgarae* and *K. robustum*, of which *K. vulgarae* is the designated type species. A group of bacteria having the above-mentioned properties does not belong to any known genera as described in Bergey's Manual of Systematic Bacteriology, and therefore belongs to a new genus.

The present invention further provides vectors which have a replicon functional in *Escherichia coli* (*E. coli*) and in *Ketogulonigenium*. *E. coli* is known to be an efficient host for amplification of a vector DNA and manipulation of recombinant DNA by simple and rapid methods. On the other hand, *Ketogulonigenium* can be used as a host for expression of *Ketogulonigenium* genes. Since the vectors of the present invention are such functional constructs, they enable cloning of certain genes of *Ketogulonigenium* in *E.*

*coli* and thereafter the effective expression of the genes in *Ketogulonigenium*. Furthermore, it is favorable that such functional constructs also contain a DNA region necessary for conjugal transfer (mob site). Hence the vectors of the present invention can first be assembled in *E. coli* and then directly introduced into *Ketogulonigenium* by conjugal mating without isolation of plasmid DNA from *E. coli*.

Polynucleotides of interest may be joined to a vector containing a selectable marker for propagation in the host. A plasmid vector can be introduced by transformation mediated by calcium chloride or other cation salts, electroporation and other transformation methods, viral or phage transduction or other methods. Such methods are described in many standard laboratory manuals, such as Davis et al., "Basic Methods in Molecular Biology," (1986), and, J. Sambrook, E. F. Fritsch and T. Maniatis (1989) "Molecular Cloning: A Laboratory Manual", $2^{nd}$ Ed.

Preferred are vectors comprising cis-acting control regions to a polynucleotide of interest. Appropriate trans acting factors may be supplied by the host, supplied by a complementing vector, or supplied by the vector itself upon introduction into the host.

In certain preferred embodiments in this regard, the vectors provide for specific expression, which may be inducible, mutant-specific and/or condition-specific. Particularly preferred among such vectors are those inducible by environmental factors that are easy to manipulate, such as temperature, nutrient additives or chemical additives. Other suitable environmental factors will be readily apparent to the skilled artisan.

Expression vectors useful in the present invention include chromosomal-, episomal-vectors e.g., vectors derived from plasmids, bacteriophage, and vectors derived from combinations thereof, such as cosmids and phagemids.

A DNA insert of interest should be operatively linked to an appropriate promoter which is preferably a host-derived promoter. Preferably, the host-derived promoter is positioned in front of a polylinker insert such that transcripts initiated at the promoter cause expression of genes cloned into the polylinker. The expression constructs can further contain sites for transcription initiation, termination and, in the transcribed region, a ribosome binding site for translation. The coding portion of the mature transcripts expressed by the constructs can include a translation initiating codon appropriate for the host at the beginning and a termination codon appropriately positioned at the end of the coding sequence to be translated.

The invention further provides the vectors of the present invention comprising a peptide fusion cloned gene expression system whereby a fused peptide serves as a tag for detecting and/or isolating the cloned gene product. The invention also provides a fused short peptide containing a biocytin residue (lysine covalently modified with a biotin), so that avidin-sepharose columns can be used to isolate the protein, and avidin-conjugated alkaline phosphatase can be used to detect the protein fusion on Western Blots.

In an additional embodiment, the DNA insert of interest additionally comprises a nucleotide sequence encoding a His-Tag sequence downstream of the promoter and polylinker, such that genes cloned into the polylinker can form translational fusions with the His-Tag. In this way, isolation of cloned proteins is facilitated because the fused His-Tag sequence allows rapid purification. A His-Tag is a polyhistidine sequence that binds to Nickel-Agarose columns, thus allowing rapid purification of the fusion protein from crude cell extracts. (Chen, B. P and Hai, T., *Gene* 139:73–79 (1994)). Removal of the His-Tag from the cloned polypeptide is achieved by treating the purified protein preparation with factor Xa or other suitable proteases.

In an additional embodiment, the DNA insert of interest additionally comprises nucleotides encoding a polypeptide. The polypeptide can be a small, immunogenic peptide sequence of about 5 to 30 amino acids, and preferably from about 10 to 20 amino acids. Ideally, this peptide sequence is not expressed natively in *Ketogulonigenium*. The DNA insert is adjacent to and translationally fused to the polylinker on either side, such that genes cloned into the polylinker are expressed as protein fusions with the immunogenic peptide. The fused peptide-antibody interaction can be used in protein isolation schemes and for detecting expression of the cloned gene fusion by immunoblotting of the expressed protein. (Enomoto, S. et al., *Biotechniques* 24:782–788 (1998)).

The invention further provides a functional gene expression vector for a periplasmic, outer membrane, or exported protein. (Payne, M. S. and Jackson, E. N., *J. Bacteriol.* 173:2278–2282 (1991)). Specifically, the invention provides a DNA insert in the vector of the insert further comprising a suitable N-terminal signal sequence from a periplasmic or exported protein gene (derived from *Ketogulonigenium* or other bacterial genera) inserted downstream of the promoter and upstream of the polylinker. In this way a periplasmic expression system is combined with easy recovery and purification of the cloned protein fusion.

The invention further provides a vector comprising a nucleotide molecule comprising a nucleotide sequence of a *Ketogulonigenium* replicon found on the endogenous plasmid of NRRL B-30035 (ADM 291-19) additionally comprising a sequence encoding a periplasmic thioredoxin-like function similar to that of the DsbA or *Pseudomonas* or *Bradyrhizobium* TlpA. The dsbA gene in *E. coli* encodes a protein that is able to catalyze formation and isomerization of disulfide bonds (Wunderlich, M. and Glockshuber, R, *J. Biol. Chem.* 268:24547–24550 (1993). Co-expression of dsbA, tlpA or the genes of functionally analagous proteins is sometimes necessary for functional expression of cloned periplasmic enzymes.

The invention further provides a vector comprising a nucleotide molecule comprising a nucleotide sequence of a *Ketogulonigenium* replicon found on the endogenous plasmid of NRRL B-30035 (ADM 291-19) additionally comprising a DNA sequence that encodes an easily isolatable protein "handle" inserted adjacent to, and in translational fusion with either side of the polylinker, such that genes cloned into the polylinker are expressed as protein fusions between the cloned protein and the vector protein handle. In this way, purification of the protein products of the cloned gene are facilitated by applying well tested purification procedures for the "protein handle." More specifically, the cloned protein follows the handle protein during the purification process. After purification, the fusion protein is then separated into its two native protein products through the application of factor Xa or other suitable protease.

In one embodiment, the vectors of the present invention comprise a cosmid site which allows for making a DNA library with about 30 kilobase inserts.

In an additional embodiment, the vectors of the present invention further comprises temperature-sensitive plasmid replication functions and regions of DNA homology to the host chromosome. The temperature sensitive replication functions allow control of integration into the homologous regions of the host chromosome through manipulation of temperature.

In one embodiment, the vectors of the present invention include two different antibiotic resistance genes inserted into two different restriction sites in the vector. One or both of the antibiotic resistance genes can carry a restriction site for gene cloning. In this way, one resistance marker is used to select transformants, and the other is used to screen for cloned DNA insertions by insertional inactivation. Suitable marker genes for the vectors of the present invention are all antibiotic resistance genes which are expressed in *E. coli* or *Ketogulonigenium*. Preferred antibiotic resistance genes include amikacin, ampicillin, chloramphenicol, erythromycin, gentamicin, kanamycin, penicillin, spectinomycin, streptomycin or tetracycline resistance genes. Particularly preferred markers include ampicillin, chloramphenicol, erythromycin, kanamycin, penicillin, spectinomycin, streptomycin, and/or tetracycline. Other suitable markers will be readily apparent to the skilled artisan.

Suitable replicons functional in *E. coli* for the vectors of the present invention can be selected from the group comprising DNA fragments containing a replicon of *E. coli*, or of any plasmid or phage which can autonomously replicate in *E. coli*. Such replicons may be isolated from the group comprising plasmids RP4, RSF1010, and pSUP301 (U.S. Pat. No. 5,399,496) lambda phages, such as phage lambda ATCC 10798, P1 phages such as P1 ATCC 25404-B1 or T-coliphages, such as coliphage T4 ATCC 11303-B4. Other suitable plasmids and replication origins will be readily apparent to the skilled artisan.

A suitable replicon functional in *Ketogulonigenium* for the vectors of the present invention is any DNA fragment which can support autonomous replication in *Ketogulonigenium*. Preferred are DNA fragments selected from the group comprising a replicon of *Ketogulonigenium* or of any plasmid, endogenous or otherwise, or phage which can autonomously replicate in *Ketogulonigenium*.

The mob site includes the origin of transfer (oriT) and acts as a recognition site for certain trans active plasmid transfer functions (R. Simon et al., *Bio/Technology* 1:784–791 (1983). A mob region is usually a mob gene and an oriT from any conjugation plasmid. The mob site can be obtained from a conjugative plasmid, e. g., plasmids RK2, RP4, RSF1010, or plasmids belonging to incompatibility groups IncP, IncQ, IncC, IncB, IncF, IncG, IncI, IncK, IncM, IncN, IncPa, IncPb, IncW, IncX, and IncZ or their derivatives. Other suitable conjugative plasmids will be readily apparent to the skilled artisan. The mob site containing plasmid can be transferred from its original host to another host with the help of tra genes by using bi-parental conjugal or tri-parental conjugal mating. The tra genes are well known as transfer genes of the broad-host-range conjugative plasmids. In the tri-parental conjugal mating, a donor strain harboring mob site-containing plasmids is mixed with a strain harboring plasmids containing tra genes, such as RP4 and RK2, and with a recipient strain. Conjugation provides an alternative method, for example, compared to transformation, of placing vectors and other genetic material into the cell. Other suitable methods will be readily apparent to the skilled artisan.

The vectors of the present invention may also comprise one or more further nucleotide molecules (also called "inserts"), for example DNA sequences having multicloning sites (also called "polylinker inserts"), expression control sequences, cos sites, terminator sequences, ribosome binding sites, DNA sequences encoding signal peptides and/or proteins, to add further desirable functions to the shuttle vector. Other suitable inserts will be readily apparent to the skilled artisan.

In more detail, the vectors of the present invention may comprise DNA sequences including one or more multicloning sites (Messing et al., *Methods in Enzymology* 101:20 (1983) derived from a variety of plasmids and phages, or from synthetic DNA sequences for convenient cloning. Suitable sources include pUC18 (Boehringer Mannheim), pUC19 (Boehringer Mannheim), M13mp8 (Boehringer Mannheim), and pBluescript. Other suitable multicloning sites will be readily apparent to the skilled artisan.

Furthermore, the vectors of the present invention may contain a wide variety of expression control sequences, such as the *E. coli* lac, trp, tac or beta-lactamase expression control system, control sequences of phage origin, such as the phage Lambda $P_L$ promoter, or expression control sequences derived from *Ketogulonigenium* strains, to name a few. Other expression control systems will be known to the skilled artisan. In addition, the shuttle vectors may contain cos sites for in vitro packaging. Furthermore, the expression constructs will further optionally contain terminator sequences for transcription, initiation, termination, natural or synthetic ribosome binding sites for effective translation, DNA sequences encoding signal peptides for efficient localization of the cloned protein(s) and structural genes of marker proteins all of which are used to construct the efficient *Ketogulonigenium* host-vector systems of the present invention.

In another embodiment, the vector of the present invention may contain an *E. coli, Ketogulonigenium*, or other promoter from a suitable gene, in front of a promoterless reporter gene, such as β-galactosidase, β-glucuronidase, green fluorescent protein or α-amylase that has a polylinker inside the reporter gene. In this way, cloned nucleic acid inserts may be screened for by inactivation of the reporter function. Other suitable reporter genes will be readily apparent to the skilled artisan.

In another embodiment, pADM291 can contain a promoterless reporter gene such as β-galactosidase, β-glucuronidase, luciferase, green fluorescent protein, α-amylase, uroporphyrinogen III methyltransferase (cobA) from *Propionibacterium freudenreichii* inserted just adjacent to an inserted polylinker, such that DNA fragments cloned into the polylinker and comprising a transcriptional promoter can cause transcription and expression of the vector reporter function in the host. In this way, cloned inserts can be screened for those containing at least a transcriptional promoter that is active in the host organism.

In another embodiment, pADM291 can contain a reporter gene, such as β-galactosidase, β-glucuronidase, green fluorescent protein or α-amylase that lacks a promoter and a translation initiation site, inserted adjacent to a polylinker such that, nucleotide fragments cloned into the polylinker and comprising a promoter and translation initiation site can form a translational fusion with the reporter function and cause expression of the reporter function in the host. In this way, cloned inserts can be screened for those containing a transcriptional promoter and translation initiation site which are active in the host organism.

The vectors of the present invention can be obtained by the following steps using the materials as described in the present description and by using recombinant DNA techniques as described in the art and known to one of ordinary skill:

(a) Preparing a nucleotide sequence containing a marker gene;

(b) Preparing a nucleotide sequence containing a replicon functional in *E. coli;*

(c) Preparing a nucleotide sequence containing a mob site;

(d) Combining the nucleotides described in (a) through (d) along with the nucleotide of the present invention by digesting the said nucleotide sequences with an appropriate restriction enzyme and ligating them to obtain the recombinant shuttle vectors of the present invention.

By these steps, the vectors containing marker genes, a replicon functional in *E. coli*, a replicon functional in *Ketogulonigenium* and a functional mob site can be constructed.

In another embodiment the pADM291 nucleotide may be fused with another vector which replicates in *E. coli, Acetobacter, Corynebacterium, Bacillus, Rhodobacter, Paracoccus, Pseudomonas, Roseobacter, Pseudogluconobacter, Gluconobacter, Serriatia, Mycobacterium*, or *Streptomyces*. Preferred is fusion with a vector which replicates in *E. coli*, such as the pET vectors, pUC18, or pUC19. Other suitable vectors will be readily apparent to the skilled artisan.

The vectors of the present invention can be transferred from *E. coli* to *Ketogulonigenium* with a very high frequency by a conjugal mating without the isolation and purification of the vector DNA. With these vectors, a genomic library constructed in *E. coli* can be transferred into *Ketogulonigenium* in one experiment. Thus, the vectors of the present invention are highly efficient in view of their simplicity in cloning experiments.

Among vectors with which the the nucleotide sequence of a *Ketogulonigenium* replicon found on the endogenous plasmid contained in Deposit No. NRRL B-30035 may be combined include pA2, pQE70, pQE60 and pQE-9, available from Qiagen; pBS vectors, Phagescript vectors, Bluescript vectors, pNH8A, pNH16a, pNH18A, pNH46A, available from Stratagene; pUC18, available from Takara Shuzo Co., Ltd.; and ptrc99a, pKK223-3, pKK233-3, pDR540, pRIT5 available from Pharmacia. Other suitable vectors will be readily apparent to the skilled artisan.

The vectors of the present invention incorporate a DNA sequence which confers upon the vector the capacity for autonomous replication in host *E. coli* cells.

The vector of the present invention may be combined with an *E. coli*-derived plasmid to create a vector which is able to replicate in both *Ketogulonigenium* and *E. coli*.

The present invention also provides a vector comprising a replicon functional in an organism selected from the genera comprising *Acetobacter, Corynebacterium, Bacillus, Rhodobacter, Paracoccus, Pseudomonas, Roseobacter, Pseudogluconobacter, Gluconobacter, Serriatia, Mycobacterium*, and *Streptomyces*. Other suitable genera will be readily apparent to the skilled artisan.

The plasmid may optionally contain its native expression vector and/or expression vectors which include chromosomal-, episomal- and virus-derived vectors, e.g., vectors derived from bacterial endogenous plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

Among known bacterial promoters suitable for use in the present invention include the *E. coli* lacI and lacZ promoters, the T3 and T7 promoters, the gpt promoter, the lambda $P_R$ and $P_L$ promoters and the trp promoter. Other suitable promoters will be readily apparent to the skilled artisan.

The invention also provides a shuttle vector comprising a *Ketogulonigenium* replicon found on the endogenous plasmid contained in Deposit No. B-30035 and at least one exogenous nucleotide sequence, wherein said shuttle vector autonomously replicates in *Ketogulonigenium* and at least one organism selected from the genera comprising *Acetobacter, Corynebacterium, Bacillus, Rhodobacter, Paracoccus, Roseobacter, Pseudomonas, Pseudogluconobacter, Gluconobacter, Serriatia, Mycobacterium*, and *Streptomyces*.

The invention also provides a method of transforming a host cell with the vectors of the present invention to obtain a stably transformed host cell. Such transformation can be effected by conjugation, including both biparental and triparental mating, transformation mediated by calcium chloride or other cation salts, electroporation and other transformation methods, transduction, or other methods. Such methods are described in many standard laboratory manuals, such as Davis et al., "Basic Methods in Molecular Biology," (1986) and J. Sambrook, E. F. Fritsch and T. Maniatis, *Molecular Cloning: A Laboratory Manual*, 2d ed., Cold Spring Harbor Laboratory Press, Cold Spring Harbor, N.Y. (1989). Preferred methods are conjugation and electroporation. Conjugation is a a process by which bacterial unilaterally transfer DNA from a donor to a recipient cell through cell to cell contact.

Suitable host cells comprise organisms selected from the genera comprising *E. coli, Ketogulonigenium, Acetobacter, Corynebacterium, Bacillus, Rhodobacter, Paracoccus, Roseobacter, Pseudomonas, Pseudogluconobacter, Gluconobacter, Serriatia, Mycobacterium*, and *Streptomyces*.

A stably transformed cell is a cell wherein a transgene (recombinant DNA) is transmitted to every successive generation. The vector transformed into the above-mentioned cells can optionally comprise a transgene. As used herein, a transgene is defined as a transplanted nucleotide sequence which is exogenous, or non-native, to the host. An exogenous nucleotide sequence, as used in the current context, is a nucleotide sequence which is not found in Deposit No. NRRL B-30035. Thus, the term exogenous nucleotide sequence is meant to encompass a nucleotide sequence that is foreign to Deposit No. NRRL B-30035, as well as a nucleotide sequence endogenous, or native, to Deposit No. NRRL B-30035 that has been modified. Modification of the endogenous nucleotide sequence may include, for instance, mutation of the native nucleotide sequence or any of its regulatory elements. As used herein, mutation is defined as any change in the wild-type sequence of genomic or plasmid DNA. An additional form of modification may also include fusion of the endogenous nucleotide sequence to a nucleotide sequence that is normally not present, in relation to the endogenous nucleotide sequence. The transgene may be regulated by its normal promoter, or more commonly, by a promoter that normally regulates a different gene. The invention also provides a method for producing transformed *Ketogulonogenium*, comprising transforming *Ketogulonigenium* with a transgene, comprising, an endogenous *Ketogulonigenium* replicon. Preferably, the endogenous *Ketogulonigenium* replicon is contained in Deposit No. NRRL B-30035. The term replicon as used herein is meant to encompass a DNA sequence comprising those genes and gene expression control elements such as promoters and terminators, other DNA sequence features such as short sequence repeats (iterons), origins of plasmid replication (ori or oriV sites), or other DNA sequence features that are required to support the autonomous replication of a circular DNA molecule in a bacterial host (Chapter 122, pp. 2295–2324, in *Escherichia coli* and *Salmonella: Cellular and Molecular Biology*, $2^{nd}$ Edition, Frederick C. Neidhardt, Ed., ASM Press (1996)). The requirements of a replicon can vary from as little as a short ori sequence in the case of plasmids that do not require their own replication proteins, to larger sequences comprising one or more plasmid-borne replication genes. The definition of a transformed cell, as used herein, is a cell where DNA has been inserted into a bacterial cell. The transformation of *Ketogulonigenium* may be transient or stable.

In an additional embodiment, the invention provides a method for producing a polypeptide comprising culturing a host cell comprising vectors of the present invention under conditions such that the polypeptide is expressed, and recovering the polypeptide. The translated polypeptide encoded by the DNA in the plasmid may be expressed in a modified form, such as a fusion protein, and may include not only secretion signals, but also additional heterologous functional regions. Thus, for instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification.

The translated protein encoded by the DNA contained in the plasmid can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Methods used and described herein are well known in the art and are more particularly described, for example, in R. F. Schleif and P. C. Wensink, *Practical Methods in Molecular Biology*, Springer-Verlag (1981); J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); M. Singer and P. Berg, *Genes & Genomes*, University Science Books, Mill Valley, Calif. (1991); J. Sambrook, E. F. Fritsch and T. Maniatis, *Molecular Cloning: A Laboratory Manual*, 2d ed., Cold Spring Harbor Laboratory Press, Cold Spring Harbor, N.Y. (1989); P. B. Kaufman et al., *Handbook of Molecular and Cellular Methods in Biology and Medicine*, CRC Press, Boca Raton, Fla. (1995); *Methods in Plant Molecular Biology and Biotechnology*, B. R. Glick and J. E. Thompson, eds. , CRC Press, Boca Raton, Fla. (1993); P. F. Smith-Keary, *Molecular Genetics of Escherichia coli*, The Guilford Press, New York, N.Y. (1989); *Plasmids: A Practical Approach*, 2nd Edition, Hardy, K. D., ed., Oxford University Press, New York, N.Y. (1993); *Vectors: Essential Data*, Gacesa, P. , and Ramji, D. P., eds., John Wiley & Sons Pub., New York, N.Y. (1994); *Guide to Electroporation and electrofusions*, Chang, D., et al., eds., Academic Press, San Diego, Calif. (1992); *Promiscuous Plasmids of Gram-Negative Bacteria*, Thomas, C. M., ed., Academic Press, London (1989); *The Biology of Plasmids*, Summers, D. K., Blackwell Science, Cambridge, Mass. (1996); *Understanding DNA and Gene Cloning: A Guide for the Curious*, Drlica, K., ed., John Wiley and Sons Pub., New York, N.Y. (1997); *Vectors: A Survey of Molecular Cloning Vectors and Their Uses*, Rodriguez, R. L., et al., eds., Butterworth, Boston, Mass. (1988); *Bacterial Conjugation*, Clewell, D. B., ed., Plenum Press, New York, N.Y. (1993); Del Solar, G., et al., "Replication and control of circular bacterial plasmids," *Microbiol. Mol. Biol. Rev.* 62:434–464 (1998); Meijer, W. J., et al., "Rolling-circle plasmids from *Bacillus subtilis*: complete nucleotide sequences and analyses of genes of pTA1015, pTA1040, pTA1050 and pTA1060, and comparisons with related plasmids from gram-positive bacteria," *FEMS Microbiol. Rev.* 21:337–368 (1998); Khan, S. A., "Rolling-circle replication of bacterial plasmids," *Microbiol. Mol. Biol. Rev.* 61:442–455 (1997); Baker, R. L., "Protein expression using ubiquitin fusion and cleavage," *Curr. Opin. Biotechnol.* 7:541–546(1996); Makrides, S. C., "Strategies for achieving high-level expression of genes in *Escherichia coli,*" *Microbiol. Rev.* 60:512–538 (1996); Alonso, J. C., et al., "Site-specific recombination in gram-positive theta-replicating plasmids," *FEMS Microbiol. Lett.* 142:1–10 (1996); Miroux, B., et al., "Over-production of protein in *Escherichia coli*: mutant hosts that allow synthesis of some membrane protein and globular protein at high levels," *J. Mol. Biol.* 260:289–298 (1996); Kurland, C. G., and Dong, H., "Bacterial growth inhibited by overproduction of protein," *Mol. Microbiol.* 21:1–4 (1996); Saki, H., and Komano, T., "DNA replication of IncQ broad-host-range plasmids in gram-negative bacteria," *Biosci. Biotechnol. Biochem.* 60:377–382 (1996); Deb, J. K., and Nath, N., "Plasmids of corynebacteria," *FEMS Microbiol. Lett.* 175: 11–20 (1999); Smith, G. P., "Filamentous phages as cloning vectors," *Biotechnol.* 10:61–83 (1988); Espinosa, M., et al., "Plasmid rolling circle replication and its control," *FEMS Microbiol. Lett.* 130:111–120 (1995); Lanka, E., and Wilkins, B. M., "DNA processing reaction in bacterial conjugation," *Ann. Rev. Biochem.* 64:141–169 (!995); Dreiseikelmann, B., "Translocation of DNA across bacterial membranes," *Microbiol. Rev.* 58:293–316 (1994); Nordstrom, K., and Wagner, E. G., "Kinetic aspects of control of plasmid replication by antisense RNA," *Trends Biochem. Sci.* 19:294–300 (1994); Frost, L. S., et al., "Analysis of the sequence gene products of the transfer region of the F sex factor," *Microbiol. Rev.* 58:162–210 (1994); Drury, L., "Transformation of bacteria by electroporation," *Methods Mol. Biol.* 58:249–256 (1996); Dower, W. J., "Electroporation of bacteria: a general approach to genetic transformation," *Genet. Eng.* 12:275–295 (1990); Na, S., et al., "The factors affecting transformation efficiency of coryneform bacteria by electroporation," *Chin. J. Biotechnol.* 11:193–198 (1995); Pansegrau, W., "Covalent association of the traI gene product of plasmid RP4 with the 5'-terminal nucleotide at the relaxation nick site," *J. Biol. Chem.* 265: 10637–10644 (1990); and Bailey, J. E., "Host-vector interactions in *Escherichia coli,*" *Adv. Biochem. Eng. Biotechnol.* 48:29–52 (1993).

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference.

EXAMPLES

Example 1

Isolation of Plasmid DNA from *Ketogulonigenium* and *E. coli* Strains.

A fresh culture of *Ketogulonigenium* strain ADM291-19 (NRRL B-30035) was grown in 10 ml X6L medium (2% Mannitol, 1% Soytone, 1% Yeast Extract, 0.5% Malt Extract, 0.5% NaCl, 0.25% K$_2$HPO$_4$, pH 7.8). A fresh culture of *E. coli* strain DH5αMCR harboring plasmid pUC19 DNA was grown in 10 ml of Luria Broth (10 g/l tryptone, 5 g/l yeast extract, 5 g/l NaCl) with 100 μg/ml ampicillin. Both cultures were incubated overnight with orbital shaking at 250 rpm at 30 degrees C. for *Ketogulonigenium* and 37 degrees C. for *E. coli*. DNA was isolated using the Promega Wizard Plus Midipreps DNA Purification System (Madison, Wis.). The culture was centrifuged at 10,000×g for 10 minutes at 4° C. in a Sorval RC-5B centrifuge using the SS-34 rotor. The pellet was suspend in 3 ml of 50 mM Tris-HCl, pH 7.5, 10 mM EDTA, 100(g/ml RnaseA. Three ml of cell lysis solution (0.2M NaOH, 1% SDS) was added and mixed by inverting the tube, then three ml of neutralization solution (1.32M potassium acetate, pH4.8) was added and mixed by inverting the tube. The lysate was centrifuged at 14,000×g for 15 minutes at 4(C in a SS-34 rotor, then the supernatant was carefully decanted to a new centrifuge tube. Ten ml of resuspension resin (40% isopropanol, 4.2M guanidine hydrochloride) was added to the supernatant fluid and mixed by swirling, then the mixture was into the Promega Wizard Midicolumn, which was connected a vacuum manifold. Vacuum was applied to pull the resin/DNA mixture completely into the midicolumn. The column was washed twice with 15 ml of column wash solution (95% ethanol, 80 mM potassium acetate, 8.3 mM Tris-HCl, pH 7.5, 40(M EDTA. The reservoir was removed from the midicolumn with a scissors, then the column was placed in a microcentrifuge tube and centrifuged at 10,000×g for 2 minutes to remove any residual solution. The midicolumn was transferred to a new microcentrifuge tube and 300 (1 of sterile dH$_2$O was applied. The tube was microcentrifuged at 10,000×g for 20 seconds to elute the DNA into solution. About 2.5 ug of pADM291 plasmid DNA was recovered. A similar procedure would be employed for other plasmids from *Ketogulonigenium* or *E. coli*, except that choice and concentration of selective antibiotics would be altered as suitable for the plasmid being isolated.

Example 2

Isolation of Strains ADM29101 and ADMX6L01, Nalidixic Acid Resistant Mutants of *Ketogulonigenium* Strains ADM291-19 (NRRL B-30035) and ADMX6L(NRRL B-21627), Respectively.

Three ml of X6L medium (2% Mannitol, 1% Soytone, 1% Yeast Extract, 0.5% Malt Extract, 0.5% NaCl, 0.25% K$_2$HPO$_4$, pH 7.8) was inoculated with strain ADM291-19 (NRRL B-30035) and the culture was grown overnight in an orbital shaker at 30 degrees C., 250 rpm. 50 uL of the overnight culture was transferred to 3 ml of X6L medium to which 1 μl of a 1% aqueous solution of Ethidium bromide had been added. This culture was incubated overnight as before. 200 μl of the second overnight culture was spread on a plate of X6L medium containing 1.3% agar plus 50 μg/ml of nalidixic acid. The plate was incubated 2–3 days at 30° C. until colonies appeared. Colonies growing on these plates were picked and naladixic acid resistant strains were purified by additional cycles of streak purification on X6L medium plates containing 50 μg/ml of nalidixic acid. A naladixic acid resistant strain was preserved as strain ADM 29101. The same procedure was used to create ADMX6L01 from ADMX6L.

Example 3

Construction of *Ketoguonigenium* Suicide Plasmid Vector pJND1000.

To invent an *E. coli*/*Ketogulonigenium* shuttle vector it was desireable that we first identify a subsequence from pADM291 that, when cloned into *E. coli* or other plasmid vectors, would support plasmid replication in *Ketogulonigenium* hosts. In order to do this, a plasmid vector that could replicate in *E. coli* and be transferred efficiently to *Ketogulonogenium*, but which cannot replicate in *Ketogulonigenium* was devised.

pJND1000 was constructed from segments of plasmids pUC19 (GenBank Accession No. M77789), pUC4K (GenBank Accession No. X06404), pFD288 (GenBank Accession No. U30830), and pFC5 (David M. Lonsdale et. al, 1995, "pFC1 to pFC7: A novel family of combinatorial cloning vectors.", Plant Molecular Biology Reporter 13[4]: 343–345).

The ampicillin resistance gene (amp$^R$) was removed from pUC19 by digesting pUC19 DNA with restriction enzymes DraI and SspI, separating the 1748 bp vector fragment from the smaller amp$^R$ fragment and other fragments by gel electrophoresis, then recovering the 1748 bp fragment from a gel slice. A kanamycin resistance gene (kan$^R$) fragment from pUC4K was prepared by digesting pUC4K with restriction enzyme PstI, treating the mixture with Klenow Fragment to produce blunt ends, separating the fragments by gel electrophoresis, then purifying the 1240 bp kan$^R$ fragment from a gel slice. The isolated fragments from pUC19 and pUC4K were mixed and ligated with T4 ligase following the protocol of GibcoBRL technical bulletin 15244-2 (Rockville, Md.) to produce "intermediate p1", an intermediate plasmid carrying pUC19 features and a kan$^R$ gene. Strain *E. coli* DH5(MCR was transformed with the ligation mixture following an established protocol ("Fresh Competent *E. coli* prepared using CaCl$_2$", pp. 1.82–1.84, in J. Sambrook, E. F. Fritsch and T. Maniatis, 1989, *Molecular Cloning: A Laboratory Manual,* 2nd Ed.). Transformants were selected on Luria Broth plates containing 50 μg/ml of kanamycin.

An oriT site for conjugative transfer was obtained from plasmid pFD288 by restricting it with HaeII, converting the single stranded ends to blunt ends by treating the mixture with Klenow Fragment, separating the fragments by agarose gel electrophoresis, then purifying the 778 bp oriT fragment from a gel slice. The intermediate p1 plasmid was opened at a single site with restriction enzyme SapI, then treated with Klenow Fragment to convert the single stranded ends to blunt ends. The SapI digested, blunt ended p1 intermediate was mixed with the purified oriT fragment, then treated with T4 ligase as above to create "intermediate p2", a plasmid which carries oriT in addition to kan$^R$ and other pUC19-derived features. Strain *E. coli* DH5αMCR was transformed with the ligation mixture as above. Intermediate p2 was confirmed by restriction digestion analysis.

The polylinker in intermediate plasmid p2 was replaced with the polylinker from pFC5. To do this the two plasmids were separately restricted with PvuII, the fragments from each digestion reaction were separated by gel electrophoresis, then the pFC5-derived polylinker fragment (531 bp), and the larger non-polylinker fragment from intermediate p2 were purified from gel slices. The recovered p2 fragment and the pFC5-derived polylinker fragment were mixed and joined using T4 ligase as above to make plasmid pJND1000. The structure of pJND1000 was confirmed by restriction digestion analysis. PJND1000 has a functioning kanamycin resistance gene, an RK2-derived oriT site to permit conjugative transfer, a polylinker for DNA cloning, forward and reverse M13 primers to facilitate DNA sequenceing reactions into the polylinker, replicates in *E. coli* strains but not in *Ketogulonigenium* strains, and permits screening for cloned inserts by inactivation of lacZα using Xgal indicator plates.

Example 4

Cloning of DNA Sequences from Plasmid pADM291 Into Suicide Vector pJND1000 to Make *E. coli/Ketogulonigenium* Shuttle Vector Candidates.

To find the functional replicon of pADM291, the Polymerase Chain Reaction (PCR) was used to generate various plasmid pADM291 DNA fragments flanked by restriction endonuclease recognition sites. These were cloned into the *Ketogulonigenium* suicide vector pJND1000 to make *Ketogulonigenium* shuttle vector candidates, which were transferred to *E. coli* hosts by plasmid transformation.

Forward and reverse oligonucleotide primers were designed with which to initiate PCR reactions using purified pADM291 DNA as substrate. The oligonucleotide primers were prepared by a commercial lab (Sigma/Genosys, The Woodlands, Tex.) using established methods known in the art. The primers had the following features ("F"=forward primer; "R"=reverse primer):

TABLE I

| Primer Label | DNA Sequence |
|---|---|
| Primer 1F | CGGAATTCGATCATATCATTCCCCAAGCGGAC |
| Primer 1R | GCTCTAGACGATGTACTCCTTGGTGCTCTCGAT |
| Primer 2F | CGGAATTCTGCTTCTTTTCGTTCGTTTCCGCC |
| Primer 2R | GCTCTAGAACATCGCTCATCTGTAGTCGCC |
| Primer 3F | CGG AATTCACAGTCAGGTGGCACATGTTCC |
| Primer 3R | CGGGATCCTGTGAAAAAGTGAGGACAGGCGGG |
| Primer 4F | CGGAATTCGGCAATGGGTCGAAATTCATAG |
| Primer 4R | CGGGATCCACGTTCCCTATTTTCCTCAATC |
| Primer 5F | CGGAATTCACACCGAAACACCTAACACGCAAG |
| Primer 5R | CGGGATCCAGTGCGGTTCACGTCATCAATG |
| Primer 6F | CGGAATTCTGCACTGCCGCTCTCGAAATG |
| Primer 6R | CGGAATTCACAAGATTGACGCAGCTCTTCGC |
| Primer 7F | CGGAATTCGGCAATGGGTCGAAATTCATAG |
| Primer 7R | CGCGGATCCACTTGTGTTGTCTTTCCC |
| Primer 8F | GCGGAATTCGACGCTGCAAACATCGAAAAC |
| Primer 8R | CGGGATCCACGTTCCCTATTTTCCTCAATC |

The PCR reactions generated pADM291 DNA fragments having the following endpoints, using the numbering of the DNA sequence in FIG. 2 (SEQ ID NO:2).

TABLE II

| PCR Fragment Label | Length | Fragment Endpoints | End Restriction Sites |
|---|---|---|---|
| PCR#1 | 2210 bp | 8060 through 1760 | 5' EcoRI-XbaI 3' |
| PCR#2 | 1523 bp | 876 through 2398 | 5' EcoRI-XbaI 3' |
| PCR#3 | 1222 bp | 2017 through 3238 | 5' EcoRI-BamHI 3' |
| PCR#4 | 2517 bp | 2955 through 5471 | 5' EcoRI-BamHI 3' |
| PCR#5 | 1965 bp | 4704 through 6668 | 5' EcoRI-BamHI 3' |
| PCR#6 | 2516 bp | 5908 through 8423 | 5' EcoRI-EcoRI 3' |
| PCR#7 | 520 bp | 2955 through 3474 | 5' EcoRI-BamHI 3' |
| PCR#8 | 1065 bp | 4407 through 5471 | 5' EcoRI-BamHI 3' |

PCR products were generated in a GENEAMP PCR System 9700 thermal cycler from Applied Biosystems using Gibco BRL Taq Polymerase (Rockville, Md.), using 35 cycles of 94° C. for 30 seconds, 60° C. for 30 seconds, 72° C. for 60 seconds. Each reaction contained 1 μl of a 50 μM solution of each primer, 10 ng of pADM291 template, 1.5 mM $MgCl_2$ and PCR Buffer supplied with the Taq Polymerase. Taq polymerase and buffer were removed from the PCR products using the Promega Wizard DNA Clean-up Kit (Madison, Wis.). The pADM291 DNA fragments from each PCR reaction were prepared for ligation into plasmid pJND1000 by reaction with the appropriate endonuclease enzymes from Gibco BRL (Rockville, Md.) as given in Table II (for example the PCR#1 products were digested with EcoRI and XbaI), followed by removal of enzyme and reaction buffer using Promega Wizard DNA Clean-up Kits. Likewise, for each PCR fragment a sample of purified plasmid pJND1000 DNA vector was digested with the same restriction enzymes that had been used to digest the PCR fragment, followed by enzyme and buffer removal using Promega Wizard DNA Clean-up Kits. Each PCR fragment was ligated into the pJND1000 vector in reactions utilizing T4 DNA ligase as in Example 3. A plasmid transformation was performed with each ligation product using competent *E. coli* strain DH5αMCR as the recipient following the transformation protocol of Example 3. Transformants were spread on Luria Broth agar plates containing 50 ug/ml of kanamycin and 40 ug/ml of Xgal and grown at 37 deg C. Colonies that were white, indicating successful insertion of a PCR fragment into the pJND1000 vector, were picked and preserved, and a sample was transferred to 1 ml of Luria Broth containing 50 ug/ml kanamycin and incubated in an orbital shaker overnight at 37 deg C., 250 rpm. Plasmid DNA was prepared from each of the grown transformant cultures by the alkaline method of H. C. Birnboim and J. Doly (Nucleic Acids Research, 7:1513–1523 (1979)). The plasmids from these cultures, each of which was a candidate for a *Ketogulonigenium* shuttle vector, were named "p291-1" for PCR product #1, "p291-2" for PCR product #2, etc. Each plasmid was confirmed to be carrying the expected PCR insert via restriction digestion and gel electrophoresis.

Example 5

Discovery of *Ketogulonigenium* Shuttle Vector p291-4 by Conjugative Transfer from *E. coli* Hosts Into *Ketogulonigenium* Hosts and Plasmid Maintainance in *Ketogulonigenium* and Bi-Parental Mating.

*Ketogulonigenium* shuttle vector plasmid candidates from Example 4 were introduced into *E. coli* strain S17-1 (ATCC 47055) by transformation, then sceened for their ability to replicate in *Ketogulonigenium* hosts after conjugative plasmid transfer from *E. coli* S17-1 to *Ketogulonigenium* strains ADM 29101 and ADM X6L01 using bi-parental matings.

A 5 ml overnight culture of each of the *E. coli* S17-1 transformants was prepared in Luria Broth containing 50 ug/ml of kanamycin with orbital shaking at 250 rpm, 37 deg C. Concurrently, 5 ml shaking overnight cultures of strains ADM X6L01 and ADM 29101 (*Ketogulonigenium robustum* and *Ketogulonigenium* sp., respectively), were prepared in X6L medium containing 50 ug/ml nalidixic acid at 30 deg C. The next day, 50 ul of each *E. coli* culture was transferred into 3 ml of fresh Luria Broth without antibiotic and grown at 37 deg C., 250 rpm until reaching an optical density of 0.1 to 0.4 at 600 nm wavelength. Likewise, 200 ul of each *Ketogulonigenium* culture was transferred to 3 ml of fresh X6L medium without antibiotic and grown at 30 deg C., 250 rpm until reaching an optical density of 0.6 at 600 nm. At this point a bi-parental mating of each *E. coli* culture with each *Ketogulonigenium* culture was prepared. 400 ul of *E. coli* culture was mixed in a sterilized 1.5 ml microcentrifuge tube with 1 ml of *Ketogulonigenium* culture. The mixed cells were pelleted in an Epindorf microcentrifuge and the supernatent was decanted. Cell pellets were suspended in 100 ul of fresh X6L medium and the entire cell suspension was spotted onto a sterile, 0.45 um×25 mm GN-6 metrical filter from Gelman Sciences (Product No. 63068), which had been placed onto the surface of a fresh X6L agar medium plate. The petri plate and filter with the cells on it was incubated overnight at 30 deg C. The mated cells were then removed from the filter by suspension in 3 ml of fresh of X6L medium. 200 ul of the cell suspension were then plated on fresh X6L medium containing 50 μg/ml kanamycin, 50 μg/ml nalidixic acid, and 1.3% Difco Bacto Agar. The plates were incubated at 30 deg C. for two days then inspected.

Matings between *E. coli* S17-1 hosts harboring plasmid p291-4 and either ADM 29101 or ADM X6L01 recipients produced more than 300 *Ketogulonigenium* transconjugant colonies on the X6L-kanamycin-naladixic acid medium plates. Matings involving any of the other shuttle plasmid candidates produced no colonies with ADM X6L 01 recipients, and 3–10 colonies with ADM 29101 recipients. The later may be attributed to recombination of the entering plasmid with the endogenous pADM291 plasmid in the case of ADM 29101 recipients, rather than to maintainance of the incoming plasmid as an independently replicating plasmid.

The identity of the p291-4 *E. coli/Ketogulonigenium* shuttle plasmid from the ADM 29101 and ADM X6L01 transconjugant strains was confirmed by restriction digestion and sequencing of plasmid DNA recovered from a transconjugant. The p291-4 shuttle vector was able to be maintained in the *Ketogulonigenium* recipient hosts. The suitability of strains ADM X6L01 and ADM29101 as conjugation recipients demonstrates that both the p291-4 shuttle vector and the transformation method is efficient with multiple species of the genus *Ketogulonigenium*. Methods analagous to those presented in the examples of this invention could be employed to derive additional shuttle vectors for use in *Ketogulonogenium*, for example, from portions of other endogenous plasmids native to other *Ketogulonigenium* strains, including but not limited to endogenous plasmids of the species *Ketogulonigenium robustum* and *Ketogulonigenium vulgarae*. The DNA sequence of PCR product #4, which corresponds to the *Ketogulonigenium* portion of p291-4, is shown in FIG. 4 (SEQ ID NO:4).

Example 6

Conjugative Transfer of Shuttle Vectors from *E. coli* Hosts into *Ketogulonigenium* Recipients Using Tri-Parental Mating.

The *E. coli* S17-1 strain that was used as the donor host in the bi-parental mating of Example 5 provides mobilization functions from a chromosomally integrated plasmid. In a tri-parental mating, plasmid-encoded mobilization functions can be provided by a third bacterial strain harboring a broad host range plasmid such as, for example, RP4 (GenBank Accession No. L27758). This would enable a broader range of bacterial strains to be used as the donor host of the shuttle plasmid that is to be conjugated into the *Ketogulonigenium* recipient. An example of a suitable third strain to be used as the source of the mobilization function in a tri-parental mating would be *E. coli* strain HB101 (ATCC 33694) transformed with RP4. An example of a non-mobilizing donor strain harboring the *Ketogulonigenium* shuttle vector would be *E. coli* HB101 transformed with an *E. coli/Ketogulonigenium* shuttle vector plasmid. The procedure would be the same as in the previous Example, except for the following modification:

Fresh liquid cultures of *Ketogulonigenium* and the shuttle vector donor strain would be prepared as in the bi-parental mating, except that *E. coli* strain HB 101 or another suitable host transformed with the shuttle vector would be used instead of the S17-1 transformant. The third strain, *E. coli* HB101 harboring RP4 for example, would be cultured in suitable medium (Luria Broth containing 5 ug/ml of tetracycline in this example, or a different antibiotic if dictated by the selectted broad host range plasmid), to an optical density of 0.1 to 0.4 at 600 nm. To prepare the mating mixture, 200–400 ul of the two non-*Ketogulonigenium* cultures would each be centrifuged to a pellet in microcentrifuge tubes. The supernatents would be decanted and the pellets would be combined and resuspended in 1.0 ml of fresh X6L medium without antibiotics, then recentrifuged to a pellet and the supernatent decanted again. This washing step in X6L medium is to prevent residual tetracycline from entering the mating mixture. Finally, 1.0 ml of the fresh culture of naladixic acid resistant *Ketogulonigenium* is added and the three cell populations are resuspended together, centrifuged to a pellet, then resuspended in 100 ul of fresh X6L medium and spotted onto the mating filter as in the bi-parental mating. The rest of the tri-parental mating is the same as in the bi-parental mating example.

Example 7

Subcloning of p291-4 to Make p291-4DS and Definition of a pADM291 Replicon.

Example 4 demonstrated that a 2517 bp DNA sequence of endogenous *Ketogulonigenium* plasmid pADM291, corresponding to the DNA sequence of FIG. 4 (SEQ ID NO:4), supports the replication of non-native circular DNA molecules in multiple *Ketogulonigenium* species. Upon examination of this sequence using programs of the "Wisconsin Package" (Genetics Computer Group [GCG], Madison, Wis., version 10.1), several open reading frames (ORFs) with protein encoding potential were discovered to exist. These correspond to FIG. 2 (SEQ ID NO:2) bases 499 through 1512 for "ORF1", encoding a 337 aa long protein, and bases 1584 through 1979 for "ORF2", encoding a 131 aa long "protein". The predicted amino acid sequences of these proteins was compared against known proteins in the PIR and SWISS-PROT databases using the GCG FASTA and BLAST programs. The results show both to be probable plasmid replication functions, showing the closest homology to other plasmid rep proteins for ORF1, and plasmid resolvase proteins for ORF2. Potential roles for these proteins include plasmid DNA replication, plasmid partitioning or plasmid mobilization, resolution of plasmid multimers, or other functions. The FIG. 4 DNA sequence includes noncoding regions of 498 bp upstream of ORF1, 70 bp between ORF1 and ORF2, and 538 bp downstream of ORF2. These non-coding regions could contain one or more plasmid replication origin sites (oriV), iterons, sequences encoding antisense RNA encoding sequences, transcriptional promoters, or other features that may participate in control of plasmid replication, partitioning, or copy number. We therefore sought to determine if the *Ketogulonigenium* functional replicon defined by PCR#4 insert of p291-4 could be made smaller by deleting various regions of p291-4 and reintroducing the smaller plasmids into *Ketogulonigenium* by biparental mating as in Example 5.

Plasmid p291-4NX had a 759 bp deletion removing DNA from the *Ketogulonigenium* NheI site to the vector polylinker XbaI site, leaving only the amino terminus of ORF1 and the noncoding region upstream of ORF1 intact. p291-4ES had a 453 bp deletion removing DNA from the *Ketogulonigenium* EcoRV site to the vector SfoI site, leaving ORF1 and ORF2 and downstream regions intact but removing DNA upstream of ORF1, perhaps including the ORF1 promoter. The plasmid p291-4DS has a 404 bp deletion removing DNA from the DraI site to the ScaI site of the *Ketogulonigenium* region, leaving ORF1 and its upstream region and ORF2 intact, but removing some but not all of the DNA downstream of ORF2. p291-4DS is able to be maintained in *E. coli*, be transferred to *Ketogulonigenium* hosts, and can replicate in *Ketogulonigenium* hosts.

This Example defines a second *E. coli*/*Ketogulonigenium* shuttle plasmid, p291-4DS, having the DNA sequence shown in FIG. 3 (SEQ ID NO:3). The DNA sequence of the *Ketogulonigenium* portion of p291-4DS, which comprises a *Ketogulonigenium* plasmid replicon, is shown in FIG. 1 (SEQ ID NO:1). It is recognized that additional DNA sequences not present in p291-4DS might participate in some aspects of pADM291 plasmid replication, plasmid multimer resolution or other maintainance functions, or plasmid partioning in *Ketogulonigenium* hosts under these or other conditions. If so, it is realized that these functions could be localized and defined using similar methods in accordance with the present invention.

Example 8

Transformation of a *Ketogulonigenium* Host Using Electroporation.

*Ketoguonigenium robustum* strain ADM X6L (NRRL B-21627) was transformed with plasmid p291-4DS using the electroporation method. Competent *Ketogulonigenium* cells were prepared by seeding a single colony of ADMX6L into 10 ml of X6L medium (1% soytone, 1% yeast extract, 0.5% malt extract, 0.5% NaCl, 0.25% K2HPO4, 2% mannitol, pH 7.8). The culture was shaken at 300 rpm at 30 C until reaching an optical density of 0.8 units at 600 nm wavelength. Five ml of this culture was used to seed 500 ml of fresh X6L medium in a 2 L baffled erlenmeyer flask, which was shook at 300 rpm at 30 C until again reaching an optical density of 0.8 units. The culture was chilled in an ice-water bath 10 minutes, then transferd to a pre-chilled centrifuge bottle and centrifuged at 5,000 rpm in a Sorvall 5C-RB Refrigerated Centrifuge for 15 minutes at 4 degrees C. Cells were maintained at 2–4 degrees C for all steps to follow. The supernatant was decanted and the cell pellet suspended in 5 ml ice-cold Milli-Q water, then additional cold Milli-Q water was was added to a volume of 500 ml. The cells were centrifuged as before, then rewashed in 500 ml of Milli-Q water as before and recentrifuged. The twice-washed cell pellet was suspended in 40 ml of ice-cold 10% glycerol then centrifuged again as before. The supernatent was decanted, then the cells were suspended in a volume of chilled 10% glycerol approximately equal to the volume of the cell pellet. The competent *Ketogulonigenium* cells were aliquoted to microcentrifuge tubes (40 ul per tube) and stored at −80 degrees C.

A BioRad "Gene Pulser II" electroporator device was set to 1.5 kV, 25 mF. The pulse controller was set to 200 ohms. One ul of p291-4DS DNA prepared as in Example 1 was added to 40 ul of thawed chilled competent *Ketogulonigenium* cells on ice. The cell-DNA mixture was transferred to a pre-chilled electroporation cuvette, which was then transferred to the electroporation device and the pulse was applied. One ml of X6L medium was added to the cuvette, then the mixture was removed, transferred to a 10-ml test tube, and incubated for 2 hours with orbital shaking at 300 rpm and 30 degrees C. The incubated cells (approximately 1.4 ml) were placed in a microcentrifuge tube and spun at 13,000 rpm for 2 minutes, after which 0.9 ml of clear supernatant was carefully removed. The cell pellet was suspended in the remaining supernatent, then the cells were spread onto the surface of an X6L medium agar plate (1.2% Difco Bacto Agar) containing 20 ug/ml of kanamycin, and the plate was incubated for 2 days at 30 degrees C. Colonies that formed on this plate were confirmed to be *Ketogulonigenium* transformed with plasmid vector p291-4DS.

All publications mentioned herein above are hereby incorporated in their entirety by reference. All publications cited in the annotations to the Genbank accession numbers or in ATCC strain descriptions cited herein are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An isolated or purified nucleic acid molecule comprising a *Ketogulonigenium* plasmid replicon as shown in SEQ ID NO: 1.

2. The nucleic acid molecule of claim 1, further comprising a replicon functional in *E. coli*.

3. The nucleic acid molecule of claim 1, further comprising a replicon functional in an organism selected from the genera consisting of *Acetobacter, Corynebacterium, Bacillus, Rhodobacter, Paracoccus, Roseobacter, Pseudomonas, Pseudogluconobacter, Gluconobacter, Serratia, Mycobacterium,* and *Streptomyces*.

4. The nucleic acid molecule of claim 1, further comprising a mob site.

5. The nucleic acid molecule of claim 4, wherein said mob site comprises a mob gene and an oriT from a conjugation plasmid.

6. The nucleic acid molecule of claim 5, wherein said conjugation plasmid is selected from plasmids which are included within the incompatibility groups consisting of IncP, IncQ, IncC, IncB, IncF, IncG, IncI, IncK, IncM, IncN, IncPa, IncPb, IncW, IncX, and IncZ.

7. The nucleic acid molecule of claim 1, further comprising a temperature-sensitive replicon.

8. The nucleic acid molecule of claim 1, further comprising at least one marker gene.

9. The nucleic acid molecule of claim 8, wherein said marker gene comprises a nucleotide sequence operative to direct synthesis of a protein conferring antibiotic resistance in a host cell population.

10. The nucleic acid molecule of claim 9, wherein said antibiotic is selected from the group comprising ampicillin, chloramphenicol, erythromycin, kanamycin, spectinomycin, streptomycin and tetracycline.

11. The nucleic acid molecule of claim 1, comprising at least one further nucleic acid sequence, wherein said further nucleic acid sequence is selected from the group consisting of a polylinker insert, an expression control sequence, a cos site, a terminator sequence, a ribosome binding site, a DNA sequence encoding a signal peptide, a DNA sequence encoding a polypeptide and a DNA sequence encoding a polypeptide containing one or more signal peptides.

12. The nucleic acid molecule of claim 11, further comprising a His-Tag sequence.

13. The nucleic acid molecule of claim 11, further comprising a nucleic acid sequence encoding a polypeptide sequence not expressed natively in *Ketogulonigenium*.

14. The nucleic acid molecule of claim 11, wherein said further nucleic acid sequence is said cos site.

15. The nucleic acid molecule of claim 1, further comprising a DNA sequence from an *E. coli*-derived plasmid.

16. The nucleic acid molecule of claim 15, wherein said *E. coli*-derived plasmid is selected from the group consisting of pET, pUC18, and pUC19.

17. The nucleic acid molecule of claim 1, further comprising a reporter gene.

18. The nucleic acid molecule of claim 17, wherein said reporter gene encodes a protein selected from the group consisting of β-galactosidase, β-glucuronidase, luciferase, green fluorescent protein α-amylase, and uroporphyrinogen III methyltransferase (cobA) from *Propionibacterium freudenreichii*.

19. The nucleic acid molecule of claim 1, wherein said nucleic acid molecule autonomously replicates in *Ketogulonigenium* and in at least one organism selected from the genera consisting of *Acetobacter, Corynebacterium, Bacillus, Rhodobacter, Paracoccus, Roseobacter, Pseudomonas, Pseudogluconobacter, Gluconobacter, Serratia, Mycobacterium*, and *Streptomyces*.

20. An isolated *Escherichia coli* cell transformed with the nucleic acid molecule of claim 1.

21. An isolated *Ketogulonigenium* cell transformed with the nucleic acid molecule of claim 1.

22. A method for producing a polypeptide, comprising culturing a host cell transformed with an isolated or purified nucleic acid molecule comprising a polynucleotide having the nucleotide sequence of a *Ketogulonigenium* plasmid replicon as shown in SEQ ID NO:1, said nucleic acid molecule comprising at least one further nucleic acid sequence, wherein said further nucleic acid sequence is selected from the group consisting of a polylinker insert, an expression control sequence, a cos site, a terminator sequence, a ribosome binding site, a DNA sequence encoding a signal peptide, a DNA sequence encoding a polypeptide and a DNA sequence encoding a polypeptide containing one or more signal peptides, under conditions such that said polypeptide is expressed, and recovering said polypeptide.

23. A method of transforming a host cell with a nucleic acid comprising:
  (a) obtaining a host cell;
  (b) transforming the host cell of (a) with an isolated or purified nucleic acid molecule comprising a polynucleotide having the nucleotide sequence of a *Ketogulonigenium* plasmid replicon as shown in SEQ ID NO:1 said nucleic acid molecule, comprising at least one further nucleic acid sequence, wherein said further nucleic acid sequence is selected from the group consisting of a polylinker insert, an expression control sequence, a cos site, a terminator sequence, a ribosome binding site, a DNA sequence encoding a signal peptide, a DNA sequence encoding a polypeptide and a DNA sequence encoding a polypeptide containing one or more signal peptides; and
  (c) obtaining a stably transformed host cell.

24. The method of claim 23, wherein said transformation comprises conjugation.

25. The method of claim 23, wherein said transformation comprises electroporation.

26. The nucleic acid molecule of claim 11, wherein said further nucleic acid sequence is said expression control sequence.

27. The nucleic acid molecule of claim 26, wherein said expression control sequence comprises an *E. coli*-derived promoter.

28. The nucleic acid molecule of claim 26, wherein said expression control sequence comprises a *Ketogulonigenium*-derived promoter.

29. The nucleic acid molecule of claim 11, wherein said further nucleic acid sequence is said polylinker insert.

30. The nucleic acid molecule of claim 11, wherein said further nucleic acid sequence is said terminator sequence.

31. The nucleic acid molecule of claim 11, wherein said further nucleic acid sequence is said ribosome binding site.

32. The nucleic acid molecule of claim 11, wherein said further nucleic acid sequence is said DNA sequence encoding a signal peptide.

33. The nucleic acid molecule of claim 11, wherein said further nucleic acid sequence is said DNA sequence encoding a polypeptide.

34. The nucleic acid molecule of claim 11, wherein said further nucleic acid sequence is said DNA sequence encoding a polypeptide containing one or more signal peptides.

35. The nucleic acid molecule of claim 1, wherein the nucleic acid sequence of the replicon is at least 96% identical over 2100 consecutive base pairs to SEQ ID NO:1.

36. The nucleic acid molecule of claim 1, wherein the nucleic acid sequence of the replicon is at least 97% identical over 2100 consecutive base pairs to SEQ ID NO:1.

37. The nucleic acid molecule of claim 1, wherein the nucleic acid sequence of the replicon is at least 98% identical over 2100 consecutive base pairs to SEQ ID NO:1.

38. The nucleic acid molecule of claim 1, wherein the nucleic acid sequence of the replicon is at least 99% identical over 2100 consecutive base pairs to SEQ ID NO:1.

39. An isolated polynucleotide comprising a *Ketogulonigenium* replicon, wherein the polynucleotide comprises a sequence at least 95% identical to nucleotides 2955–4960 of SEQ ID NO:2, immediately followed by a sequence at least 95% identical to nucleotides 2955–4960 of SEQ ID NO:2.

40. A shuttle vector that has at least 95% sequence identity to SEQ ID NO:3.

41. The shuttle vector of claim 40, wherein the shuttle vector has at least 97% sequence identity to SEQ ID NO:3.

42. The shuttle vector of claim 40, wherein the shuttle vector has at least 99% sequence identity to SEQ ID NO:3.

43. A shuttle vector comprising the nucleic acid sequence of SEQ ID NO:3.

44. The nucleic acid molecule of claim 2, wherein said nucleic acid molecule autonomously replicates in *Ketogulonigenium* and *E. coli*.

45. The nucleic acid molecule of claim 35, wherein said nucleic acid molecule autonomously replicates in *Ketogulonigenium* and *E. coli*.

46. The nucleic acid molecule of claim 39, wherein said nucleic acid molecule autonomously replicates in *Ketogulonigenium* and *E. coli*.

47. The nucleic acid molecule of claim 40, wherein said nucleic acid molecule autonomously replicates in *Ketogulonigenium* and *E. coil*.

* * * * *

UNITED STATES PATENT AND TRADEMARK OFFICE
CERTIFICATE OF CORRECTION

| | | |
|---|---|---|
| PATENT NO. | : 7,033,824 B2 | |
| APPLICATION NO. | : 09/826206 | |
| DATED | : April 25, 2006 | |
| INVENTOR(S) | : John D'Elia | |

It is certified that error appears in the above-identified patent and that said Letters Patent is hereby corrected as shown below:

Column 1, line 46-47, delete "in an attempt increase production" and substitute --in an attempt to increase production-- therefor Column 7, line 36, delete "(oriT) and acts" and substitute --(*oriT*) and acts-- therefor Column 7, line 39, delete "A mob region is usually a mob gene and an oriT from" and substitute --A mob region is usually a *mob* gene and an *oriT* from-- therefor Column 7, line 48, delete "help of tra genes by" and substitute --help of *tra* genes by-- therefor Column 7, line 49, delete "The tra genes are well known" and substitute --the *tra* genes are well known-- therefor Column 7, line 53, delete "plasmids containing tra genes, such" and substitute --plasmids containing *tra* genes, such-- therefor Column 8, line 12, delete "as the *E. coli* lac, trp, tac or" and substitute --as the *E. coli lac, trp, tac* or-- therefor Column 12, line 26, delete "conjugation." *Ann. Rev. Biochem.* 64:141-169 (!995)" and substitute --conjugation. *Ann. Rev. Biochem.* 64:141-169 (1995)-- therefor Column 15, line 4, delete "reverse M13 primers to facilitate DNA sequenceing" and substitute --reverse M13 primers to facilitate DNA sequencing-- therefor Column 18, line 24, delete "the selectted broad range" and substitute --the selected broad range-- therefor

UNITED STATES PATENT AND TRADEMARK OFFICE
CERTIFICATE OF CORRECTION

PATENT NO. : 7,033,824 B2
APPLICATION NO. : 09/826206
DATED : April 25, 2006
INVENTOR(S) : John D'Elia It is certified that error appears in the above-identified patent and that said Letters Patent is hereby corrected as shown below:

Column 20, line 6, delete "ice-water bath 10 minutes, then transferd to a"
and substitute --ice-water bath 10 minutes, then transferred to a-- therefor Signed and Sealed this Fourteenth Day of October, 2008

JON W. DUDAS
*Director of the United States Patent and Trademark Office*